US012428457B2

(12) United States Patent
Webster

(10) Patent No.: US 12,428,457 B2
(45) Date of Patent: Sep. 30, 2025

(54) COLD-SHOCK PROTEIN SCAFFOLD FOR ENGINEERING NON-ANTIBODY BINDING PROTEINS

(71) Applicant: University of South Florida, Tampa, FL (US)

(72) Inventor: Jack Mathew Webster, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 823 days.

(21) Appl. No.: 17/589,049

(22) Filed: Jan. 31, 2022

(65) Prior Publication Data
US 2022/0242923 A1 Aug. 4, 2022

Related U.S. Application Data

(60) Provisional application No. 63/199,885, filed on Jan. 29, 2021.

(51) Int. Cl.
C07K 14/47 (2006.01)
C07K 14/195 (2006.01)

(52) U.S. Cl.
CPC ............ C07K 14/47 (2013.01); C07K 14/195 (2013.01); C07K 2319/00 (2013.01)

(58) Field of Classification Search
CPC .. C07K 14/47; C07K 14/195; C07K 2319/00; C12R 2001/01
See application file for complete search history.

(56) References Cited

U.S. PATENT DOCUMENTS

| | | | |
|---|---|---|---|
| 4,429,008 A | 1/1984 | Martin et al. | |
| 4,489,710 A | 12/1984 | Spitler | |
| 4,507,234 A | 3/1985 | Kato et al. | |
| 4,569,789 A | 2/1986 | Blattler et al. | |
| 4,625,014 A | 11/1986 | Senter et al. | |
| 4,638,045 A | 1/1987 | Kohn et al. | |
| 4,671,958 A | 6/1987 | Rodwell et al. | |
| 4,673,562 A | 6/1987 | Davison et al. | |
| 4,699,784 A | 10/1987 | Shih et al. | |
| 4,873,088 A | 10/1989 | Mayhew et al. | |
| 5,057,313 A | 10/1991 | Shih et al. | |
| 5,156,840 A | 10/1992 | Goers et al. | |
| 5,709,846 A | 1/1998 | Lem et al. | |
| 5,733,522 A | 3/1998 | Schmitt-Willich et al. | |
| 8,853,494 B2 * | 10/2014 | Bonin et al. ......... | C07K 14/195 800/298 |
| 9,388,244 B2 | 7/2016 | Marks et al. | |
| 9,469,670 B2 | 10/2016 | Abrahmsén et al. | |
| 10,556,933 B2 | 2/2020 | Abrahmsén et al. | |
| 2007/0105113 A1 * | 5/2007 | Sagawa et al. .......... | C12N 9/22 435/6 |

FOREIGN PATENT DOCUMENTS

| | | | |
|---|---|---|---|
| EP | 3473647 | 4/2019 | |
| WO | WO2008068637 A2 * | 6/2008 | |
| WO | WO2013134880 A1 * | 9/2013 | ............. C12N 15/63 |
| WO | WO2018170324 A1 * | 9/2018 | ............... C07K 7/00 |

OTHER PUBLICATIONS

Von König K, Kachel N, Kalbitzer HR, Kremer W. RNA and DNA Binding Epitopes of the Cold Shock Protein TmCsp from the Hyperthermophile Thermotoga maritima. 2020. Protein J. Oct. 2020;39(5):487-500. (Year: 2020).*

Nygren PA, Skerra A. Binding proteins from alternative scaffolds. J Immunol Methods. Jul. 2004;290(1-2):3-28. (Year: 2004).*

Peters Daniel T., et al. Human Lin28 Forms a High-Affinity 1:1 Complex with the 106-363 Cluster miRNA miR-36. Biochemistry 2016 55 (36), 5021-5027 (Year: 2016).*

Baker, J. D., Shelton, L. B., Zheng, D., Favretto, F., Nordhues, B. A., Darling, A., Sullivan, L. E., Sun, Z., Solanki, P. K., Martin, M. D., Suntharalingam, A., Sabbagh, J. J., Becker, S., Mandelkow, E., Uversky, V. N., Zweckstetter, M., Dickey, C. A., Koren, J., and Blair, L. J. (2017) Human cyclophilin 40 unravels neurotoxic amyloids. PLoS Biol. 15, e2001336.

Bauer, P. O., Goswami, A., Wong, H. K., Okuno, M., Kurosawa, M., Yamada, M., Miyazaki, H., Matsumoto, G., Kino, Y., Nagai, Y., and Nukina, N. (2010) Harnessing chaperone-mediated autophagy for the selective degradation of mutant huntingtin protein. Nat Biotech. 28, 256-263.

Binder, L. I., Frankfurter, A., and Rebhun, L. I. (1985) The distribution of tau in the mammalian central nervous system. J. Cell Biol. 101, 1371-1378.

Blair, L. J., Nordhues, B. A., Hill, S. E., Scaglione, K. M., O'Leary, J. C., Fontaine, S. N., Breydo, L., Zhang, B., Li, P., Wang, L., Cotman, C., Paulson, H. L., Muschol, M., Uversky, V. N., Klengel, T., Binder, E. B., Kayed, R., Golde, T. E., Berchtold, N., and Dickey, C. A. (2013) Accelerated neurodegeneration through chaperone-mediated oligomerization of tau. J Clin Invest. 123, 4158-4169.

Bloom, G. S. (2014) Amyloid-β and tau: the trigger and bullet in Alzheimer disease pathogenesis. JAMA Neurol. 71, 505-508.

Boder, E. T., & Wittrup, K. D. (1997). Yeast surface display for screening combinatorial polypeptide libraries. Nature biotechnology, 15(6), 553-557.

Boutajangout, A., Quartermain, D., and Sigurdsson, E. M. (2010) Immunotherapy targeting pathological tau prevents cognitive decline in a new tangle mouse model. J Neurosci. 30, 16559-16566.

Cardenas-Aguayo, M. del C., Gomez-Virgilio, L., DeRosa, S., and Meraz-Rios, M. A. (2014) The Role of Tau Oligomers in the Onset of Alzheimer's Disease Neuropathology. ACS Chem. Neurosci. 5, 1178-1191.

Castillo-Carranza, D. L., Gerson, J. E., Sengupta, U., Guerrero-Munoz, M. J., Lasagna-Reeves, C. A., and Kayed, R. (2014) Specific Targeting of Tau Oligomers in Htau Mice Prevents Cognitive Impairment and Tau Toxicity Following Injection with Brain-Derived Tau Oligomeric Seeds. Journal of Alzheimer's Disease. 40, S97-S111.

(Continued)

Primary Examiner — Misook Yu
Assistant Examiner — James Lyle McLellan
(74) Attorney, Agent, or Firm — Meunier Carlin & Curfman LLC

(57) ABSTRACT

Disclosed herein are compositions and methods directed to non-antibody protein scaffolds derived from cold-shock proteins.

13 Claims, 16 Drawing Sheets
Specification includes a Sequence Listing.

(56) References Cited

OTHER PUBLICATIONS

Chai, X., Wu, S., Murray, T. K., Kinley, R., Cella, C. V., Sims, H., Buckner, N., Hanmer, J., Davies, P., O'Neill, M. J., Hutton, M. L., and Citron, M. (2011) Passive Immunization with Anti-Tau Antibodies in Two Transgenic Models Reduction of Tau Pathology and Delay of Disease Progression. J. Biol. Chem. 286, 34457-34467.
Cheng, Z., De Jesus, O. P., Kramer, D. J., De, A., Webster, J. M., Gheysens, O., Levi, J., Namavari, M., Wang, S., Park, J. M., Zhang, R., Liu, H., Lee, B., Syud, F. A., and Gambhir, S. S. (2010) 64Cu-labeled affibody molecules for imaging of HER2 expressing tumors. Mol Imaging Biol. 12, 316-324.
Cheng, Z., De Jesus, O. P., Namavari, M., De, A., Levi, J., Webster, J. M., Zhang, R., Lee, B., Syud, F. A., and Gambhir, S. S. (2008) Small-animal PET imaging of human epidermal growth factor receptor type 2 expression with site-specific 18F-labeled protein scaffold molecules. J. Nucl. Med. 49, 804-813.
Cherf, G. M., and Cochran, J. R. (2015) Applications of yeast surface display for protein engineering. Methods Mol Biol. 1319, 155-175.
Clavaguera, F., Bolmont, T., Crowther, R. A., Abramowski, D., Frank, S., Probst, A., Fraser, G., Stalder, A. K., Beibel, M., Staufenbiel, M., Jucker, M., Goedert, M., and Tolnay, M. (2009) Transmission and spreading of tauopathy in transgenic mouse brain. Nat. Cell Biol. 11, 909-913.
Cleary, J. P., Walsh, D. M., Hofmeister, J. J., Shankar, G. M., Kuskowski, M. A., Selkoe, D. J., and Ashe, K. H. (2005) Natural oligomers of the amyloid-beta protein specifically disrupt cognitive function. Nat. Neurosci. 8, 79-84.
Cohen, T. J., Guo, J. L., Hurtado, D. E., Kwong, L. K., Mills, I. P., Trojanowski, J. Q., and Lee, V. M. Y. (2011) The acetylation of tau inhibits its function and promotes pathological tau aggregation. Nat Commun. 2, 252.
Colby, D. W., Chu, Y., Cassady, J. P., Duennwald, M., Zazulak, H., Webster, J. M., Messer, A., Lindquist, S., Ingram, V. M., and Wittrup, K. D. (2004) Potent inhibition of huntingtin aggregation and cytotoxicity by a disulfide bond-free single-domain intracellular antibody. Proc. Natl. Acad. Sci. U.S.A. 101, 17616-17621.
Colby, D. W., Garg, P., Holden, T., Chao, G., Webster, J. M., Messer, A., Ingram, V. M., and Wittrup, K. D. (2004) Development of a human light chain variable domain (V(L)) intracellular antibody specific for the amino terminus of huntingtin via yeast surface display. J. Mol. Biol. 342, 901-912.
Collin, L., Bohrmann, B., Gopfert, U., Oroszlan-Szovik, K., Ozmen, L., and Gruninger, F. (2014) Neuronal uptake of tau/pS422 antibody and reduced progression of tau pathology in a mouse model of Alzheimer's disease. Brain. 137, 2834-2846.
Ferrigno, Paul Ko. "Non-antibody protein-based biosensors." Essays in biochemistry 60.1 (2016): 19-25.
Fiedler, M., and Skerra, A. (2014) Non-Antibody Scaffolds as Alternative Therapeutic Agents. In Handbook of Therapeutic Antibodies (Dubel, S., and Reichert, J. M. eds), pp. 435-474, Wiley-VCH Verlag GmbH & Co. KGaA, 10.1002/9783527682423.ch17.
Fitzpatrick, A. W. P., Falcon, B., He, S., Murzin, A. G., Murshudov, G., Garringer, H. J., Crowther, R. A., Ghetti, B., Goedert, M., and Scheres, S. H. W. (2017) Cryo-EM structures of tau filaments from Alzheimer's disease. Nature. 547, 185-190.
Francisco, Joseph A., Rob Campbell, Brent L. Iverson, and George Georgiou. "Production and fluorescence-activated cell sorting of Escherichia coli expressing a functional antibody fragment on the external surface." Proceedings of the National Academy of Sciences 90, No. 22 (1993): 10444-10448.
Frenkel-Pinter, M., Richman, M., Belostozky, A., Abu-Mokh, A., Gazit, E., Rahimipour, S., and Segal, D. (2016) Selective Inhibition of Aggregation and Toxicity of a Tau-Derived Peptide using Its Glycosylated Analogues. Chemistry. 22, 5945-5952.
Frenkel-Pinter, M., Tal, S., Scherzer-Attali, R., Abu-Hussien, M., Alyagor, I., Eisenbaum, T., Gazit, E., and Segal, D. (2017) C1-NQTrp Alleviates Tauopathy Symptoms in a Model Organism through the Inhibition of Tau Aggregation-Engendered Toxicity. Neurodegener Dis. 17, 73-82.
Fuchs, P. F. J., and Alix, A. J. P. (2005) High accuracy prediction of β-turns and their types using propensities and multiple alignments. Proteins. 59, 828-839.
Ganguly, P., Do, T. D., Larini, L., LaPointe, N. E., Sercel, A. J., Shade, M. F., Feinstein, S. C., Bowers, M. T., and Shea, J.-E. (2015) Tau Assembly: The Dominant Role of PHF6 (VQIVYK) in Microtubule Binding Region Repeat R3. J Phys Chem B. 119, 4582-4593.
Georgiou, G., Stathopoulos, C., Daugherty, P. S., Nayak, A. R., & Iverson, B. L. (1997). Display of heterologous proteins on the surface of microorganisms: from the screening of combinatorial libraries to live recombinant vaccines. Nature biotechnology, 15(1), 29-34.
Gerson, J. E., Sengupta, U., and Kayed, R. (2017) Tau Oligomers as Pathogenic Seeds: Preparation and Propagation In Vitro and In Vivo. Methods Mol. Biol. 1523, 141-157.
Gu, J., Congdon, E. E., and Sigurdsson, E. M. (2013) Two Novel Tau Antibodies Targeting the 396/404 Region Are Primarily Taken Up by Neurons and Reduce Tau Protein Pathology. J. Biol. Chem. 288, 33081-33095.
Guidotti, G., Brambilla, L., and Rossi, D. (2017) Cell-Penetrating Peptides: From Basic Research to Clinics. Trends in Pharmacological Sciences. 38, 406-424.
Hanes, Jozef, and Andreas Plückthun. "In vitro selection and evolution of functional proteins by using ribosome display." Proceedings of the National Academy of Sciences 94.10 (1997): 4937-4942.
Heinemann, U., & Roske, Y. (2021). Cold-shock domains—abundance, structure, properties, and nucleic-acid binding. Cancers, 13(2), 190.
Hoffman, R. M. "In vivo imaging of metastatic cancer with fluorescent proteins." Cell death and differentiation 9.8 (2002): 786-789.
Hosse, Ralf J., Achim Rothe, and Barbara E. Power. "A new generation of protein display scaffolds for molecular recognition." Protein Science 15.1 (2006): 14-27.
Huang, X., and Zhou, H.-X. (2006) Similarity and Difference in the Unfolding of Thermophilic and Mesophilic Cold Shock Proteins Studied by Molecular Dynamics Simulations. Biophysical Journal. 91, 2451-2463.
Huber, R., Langworthy, T. A., Konig, H., Thomm, M., Woese, C. R., Sleytr, U. B., and Stetter, K. O. (1986) *Thermotoga maritima* sp. nov. represents a new genus of unique extremely thermophilic eubacteria growing up to 90° C. Arch. Microbiol. 144, 324-333.
Hurtado, D. E., Molina-Porcel, L., Iba, M., Aboagye, A. K., Paul, S. M., Trojanowski, J. Q., and Lee, V. M.-Y. (2010) A{beta} accelerates the spatiotemporal progression of tau pathology and augments tau amyloidosis in an Alzheimer mouse model. Am. J. Pathol. 177, 1977-1988.
Ising, C., Gallardo, G., Leyns, C. E. G., Wong, C. H., Stewart, F., Koscal, L. J., Roh, J., Robinson, G. O., Serrano, J. R., and Holtzman, D. M. (2017) AAV-mediated expression of anti-tau scFvs decreases tau accumulation in a mouse model of tauopathy. Journal of Experimental Medicine. 10.1084/jem.20162125.
Jansson, M., Hallén, D., Koho, H., Andersson, G., Berghard, L., Heidrich, J., . . . & Kö, J. (1997). Characterization of ligand binding of a soluble human insulin-like growth factor I receptor variant suggests a ligand-induced conformational change. Journal of Biological Chemistry, 272(13), 8189-8197.
Karatan, E., Han, Z., and Kay, B. (2006) Molecular Display Technologies. in Reviews in Cell Biology and Molecular Medicine, Wiley-VCH Verlag GmbH & Co. KGaA, 10.1002/3527600906.mcb.200400086.
Kaushik, S., and Cuervo, A. M. (2012) Chaperone-mediated autophagy: a unique way to enter the lysosome world. Trends Cell Biol. 22, 407-417.
Keefe, Anthony D., and Jack W. Szostak. "Functional proteins from a random-sequence library." Nature 410.6829 (2001): 715-718.
Koga, H., Martinez-Vicente, M., Macian, F., Verkhusha, V. V., and Cuervo, A. M. (2011) A photoconvertible fluorescent reporter to track chaperone-mediated autophagy. Nat Commun. 2, 386.

(56) References Cited

OTHER PUBLICATIONS

Kowall, N. W., and Kosik, K. S. (1987) Axonal disruption and aberrant localization of tau protein characterize the neuropil pathology of Alzheimer's disease. Ann. Neurol. 22, 639-643.

Kremer, W. et al. Solution NMR structure of the cold-shock protein from the hyperthermophilic bacterium *Thermotoga maritima*. Eur. J. Biochem. 268, 2527-2539 (2001).

Krishnaswamy, S., Lin, Y., Rajamohamedsait, W. J., Rajamohamedsait, H. B., Krishnamurthy, P., and Sigurdsson, E. M. (2014) Antibody-derived in vivo imaging of tau pathology. J. Neurosci. 34, 16835-16850.

Lasagna-Reeves, C. A., Castillo-Carranza, D. L., Sengupta, U., Guerrero-Munoz, M. J., Kiritoshi, T., Neugebauer, V., Jackson, G. R., and Kayed, R. (2012) Alzheimer brain-derived tau oligomers propagate pathology from endogenous tau. Scientific Reports. 2, 700.

Lee, S., and Shea, T. B. (2012) Caspase-Mediated Truncation of Tau Potentiates Aggregation. International Journal of Alzheimer's Disease. 2012, e731063.

Leroy, K., Ando, K., Laporte, V., Dedecker, R., Suain, V., Authelet, M., Heraud, C., Pierrot, N., Yilmaz, Z., Octave, J.-N., and Brion, J.-P. (2012) Lack of tau proteins rescues neuronal cell death and decreases amyloidogenic processing of APP in APP/PS1 mice. Am. J. Pathol. 181, 1928-1940.

Levites, Y., Golde, T., Cruz, P. E., Rosario, A. M., and Sinyavskiy, G. D. (2015) Functionalized intrabodies as potential tau targeting therapy. Alzheimer's & Dementia: The Journal of the Alzheimer's Association. 11, P227.

Lindquist, J. A. & Mertens, P. R. Cold shock proteins: from cellular mechanisms to pathophysiology and disease. Cell Commun. Signal. 16, 63 (2018).

Lipovsek, Dasa, and Andreas Plückthun. "In-vitro protein evolution by ribosome display and mRNA display." Journal of immunological methods 290.1-2 (2004): 51-67.

Lippens, G., Sillen, A., Landrieu, I., Amniai, L., Sibille, N., Barbier, P., Leroy, A., Hanoulle, X., and Wieruszeski, J.-M. (2007) Tau Aggregation in Alzheimer's Disease. Prion. 1, 21-25.

Lofblom, J., Feldwisch, J., Tolmachev, V., Carlsson, J., Stahl, S., and Frejd, F. Y. (2010) Affibody molecules: Engineered proteins for therapeutic, diagnostic and biotechnological applications. FEBS Letters. 584, 2670-2680.

Meraz-Rios, M. A., Lira-De Leon, K. I., Campos-Pena, V., De Anda-Hernandez, M. A., and Mena- Lopez, R. (2010) Tau oligomers and aggregation in Alzheimer's disease. Journal of Neurochemistry. 112, 1353-1367.

Miao, Z., Ren, G., Jiang, L., Liu, H., Webster, J. M., Zhang, R., Namavari, M., Gambhir, S. S., Syud, F., and Cheng, Z. (2011) A novel 18F-labeled two-helix scaffold protein for PET imaging of HER2-positive tumor. Eur. J. Nucl. Med. Mol. Imaging. 38, 1977-1984.

Miersch, S., and Sidhu, S. S. (2016) Intracellular targeting with engineered proteins. F1000Res. 10.12688/f1000research.8915.1.

Motono, C., Gromiha, M. M., and Kumar, S. (2008) Thermodynamic and kinetic determinants of Thermotoga maritima cold shock protein stability: A structural and dynamic analysis. Proteins. 71, 655-669.

Naldini, L. (2015) Gene therapy returns to centre stage. Nature. 526, 351-360.

Neri, Dario, Silvia Montigiani, and Perry M. Kirkham. "Biophysical methods for the determination of antibody-antigen affinities." Trends in Biotechnology 14, No. 12 (1996): 465-470.

Ng, K. P., Pascoal, T. A., Mathotaarachchi, S., Therriault, J., Kang, M. S., Shin, M., Guiot, M.-C., Guo, Q., Harada, R., Comley, R. A., Massarweh, G., Soucy, J.-P., Okamura, N., Gauthier, S., and Rosa-Neto, P. (2017) Monoamine oxidase B inhibitor, selegiline, reduces 18F-THK5351 uptake in the human brain. Alzheimer's Research & Therapy. 9, 25.

Nussbaum, J. M., Schilling, S., Cynis, H., Silva, A., Swanson, E., Wangsanut, T., Tayler, K., Wiltgen, B., Hatami, A., Ronicke, R., Reymann, K., Hutter-Paier, B., Alexandru, A., Jagla, W., Graubner, S., Glabe, C. G., Demuth, H.-U., and Bloom, G. S. (2012) Prion-like behaviour and tau-dependent cytotoxicity of pyroglutamylated amyloid-β. Nature. 485, 651-655.

Owens, B. (2017) Faster, deeper, smaller—the rise of antibody-like scaffolds. Nature Biotechnology. 35, nbt0717-602-602.

Ozawa, M., Ohashi, K., & Onuma, M. (2005). Identification and characterization of peptides binding to newcastle disease virus by phage display. Journal of veterinary medical science, 67(12), 1237-1241.

Patterson, K. R., Remmers, C., Fu, Y., Brooker, S., Kanaan, N. M., Vana, L., Ward, S., Reyes, J. F., Philibert, K., Glucksman, M. J., and Binder, L. I. (2011) Characterization of prefibrillar Tau oligomers in vitro and in Alzheimer disease. J. Biol. Chem. 286, 23063-23076.

Pedersen, J. T., and Sigurdsson, E. M. (2015) Tau immunotherapy for Alzheimer's disease. Trends Mol Med. 21, 394-402.

Peeraer, E., Bottelbergs, A., Van Kolen, K., Stancu, I.-C., Vasconcelos, B., Mahieu, M., Duytschaever, H., Ver Donck, L., Torremans, A., Sluydts, E., Van Acker, N., Kemp, J. A., Mercken, M., Brunden, K. R., Trojanowski, J. Q., Dewachter, I., Lee, V. M. Y., and Moechars, D. (2015) Intracerebral injection of preformed synthetic tau fibrils initiates widespread tauopathy and neuronal loss in the brains of tau transgenic mice. Neurobiol. Dis. 73, 83-95.

Peretti, D., Bastide, A., Radford, H., Verity, N., Molloy, C., Martin, M. G., Moreno, J. A., Steinert, J. R., Smith, T., Dinsdale, D., Willis, A. E., and Mallucci, G. R. (2015) RBM3 mediates structural plasticity and protective effects of cooling in neurodegeneration. Nature. 518, 236-239.

Permyakov, S. E., Permyakov, E. A., and Uversky, V. N. (2015) Intrinsically disordered caldesmon binds calmodulin via the "buttons on a string" mechanism. PeerJ. 3, e1265.

Phadtare, S., Hwang, J., Severinov, K., and Inouye, M. (2003) CspB and CspL, thermostable coldshock proteins from Thermotoga maritima. Genes Cells. 8, 801-810.

Rapoport, M., Dawson, H. N., Binder, L. I., Vitek, M. P., and Ferreira, A. (2002) Tau is essential to beta-amyloid-induced neurotoxicity. Proc. Natl. Acad. Sci. U.S.A. 99, 6364-6369.

Ren, G., Webster, J. M., Liu, Z., Zhang, R., Miao, Z., Liu, H., Gambhir, S. S., Syud, F. A., and Cheng, Z. (2012) In vivo targeting of HER2-positive tumor using 2-helix affibody molecules. Amino Acids. 43, 405-413.

Ren, G., Zhang, R., Liu, Z., Webster, J. M., Miao, Z., Gambhir, S. S., Syud, F. A., and Cheng, Z. (2009) A 2-helix small protein labeled with 68Ga for PET imaging of HER2 expression. J. Nucl. Med. 50, 1492-1499.

Roberson, E. D., Scearce-Levie, K., Palop, J. J., Yan, F., Cheng, I. H., Wu, T., Gerstein, H., Yu, G.-Q., and Mucke, L. (2007) Reducing endogenous tau ameliorates amyloid beta-induced deficits in an Alzheimer's disease mouse model. Science. 316, 750-754.

Roberts, R. W., & Szostak, J. W. (1997). RNA-peptide fusions for the in vitro selection of peptides and proteins. Proceedings of the National Academy of Sciences, 94(23), 12297-12302.

Ruoslahti, Erkki. "RGD and other recognition sequences for integrins." Annual review of cell and developmental biology 12:697-715, 1996.

Saint-Aubert, L., Lemoine, L., Chiotis, K., Leuzy, A., Rodriguez-Vieitez, E., and Nordberg, A. (2017) Tau PET imaging: present and future directions. Molecular Neurodegeneration. 12, 19.

Sankaranarayanan, S., Barten, D. M., Vana, L., Devidze, N., Yang, L., Cadelina, G., Hoque, N., DeCarr, L., Keenan, S., Lin, A., Cao, Y., Snyder, B., Zhang, B., Nitla, M., Hirschfeld, G., Barrezueta, N., Polson, C., Wes, P., Rangan, V. S., Cacace, A., Albright, C. F., Meredith, J., Trojanowski, J. Q., Lee, V. M.-Y., Brunden, K. R., and Ahlijanian, M. (2015) Passive immunization with phospho-tau antibodies reduces tau pathology and functional deficits in two distinct mouse tauopathy models. PLoS ONE. 10, e0125614.

Santacruz, K., Lewis, J., Spires, T., Paulson, J., Kotilinek, L., Ingelsson, M., Guimaraes, A., DeTure, M., Ramsden, M., McGowan, E., Forster, C., Yue, M., Orne, J., Janus, C., Mariash, A., Kuskowski, M., Hyman, B., Hutton, M., and Ashe, K. H. (2005) Tau suppression in a neurodegenerative mouse model improves memory function. Science. 309, 476-481.

(56) References Cited

OTHER PUBLICATIONS

Seidler, P., Boyer, D., Rodriguez, J., Sawaya, M., Cascio, D., Murray, K., Gonen, T., and Eisenberg, D. (2018) Structure-based inhibitors of tau aggregation. Nat Chem. 10, 170-176.

Shelton, L. B., Baker, J. D., Zheng, D., Sullivan, L. E., Solanki, P. K., Webster, J. M., Sun, Z., Sabbagh, J. J., Nordhues, B. A., Koren, J., Ghosh, S., Blagg, B. S. J., Blair, L. J., and Dickey, C. A. (2017) Hsp90 activator Aha1 drives production of pathological tau aggregates. Proc. Natl. Acad. Sci. U.S.A. 114, 9707-9712.

Shipton, O. A., Leitz, J. R., Dworzak, J., Acton, C. E. J., Tunbridge, E. M., Denk, F., Dawson, H. N., Vitek, M. P., Wade-Martins, R., Paulsen, O., and Vargas-Caballero, M. (2011) Tau protein is required for amyloid {beta}-induced impairment of hippocampal long-term potentiation. J. Neurosci. 31, 1688-1692.

Sigurdsson, E. M. (2016) Tau Immunotherapy. NDD. 16, 34-38.

Simonato, M., Bennett, J., Boulis, N. M., Castro, M. G., Fink, D. J., Goins, W. F., Gray, S. J., Lowenstein, P. R., Vandenberghe, L. H., Wilson, T. J., Wolfe, J. H., and Glorioso, J. C. (2013) Progress in gene therapy for neurological disorders. Nat Rev Neurol. 9, 277-291.

Tych, K. M., Batchelor, M., Hoffmann, T., Wilson, M. C., Hughes, M. L., Paci, E., Brockwell, D. J., and Dougan, L. (2016) Differential Effects of Hydrophobic Core Packing Residues for Thermodynamic and Mechanical Stability of a Hyperthermophilic Protein. Langmuir. 32, 7392-7402.

Visintin, M., Settanni, G., Maritan, A., Graziosi, S., Marks, J. D., and Cattaneo, A. (2002) The intracellular antibody capture technology (IACT): towards a consensus sequence for intracellular antibodies11Edited by J. Karn. Journal of Molecular Biology. 317, 73-83.

Von Bergen, M., Barghorn, S., Li, L., Marx, A., Biernat, J., Mandelkow, E. M., and Mandelkow, E. (2001) Mutations of tau protein in frontotemporal dementia promote aggregation of paired helical filaments by enhancing local beta-structure. J. Biol. Chem. 276, 48165-48174.

Walsh, D. M., Klyubin, I., Fadeeva, J. V., Cullen, W. K., Anwyl, R., Wolfe, M. S., Rowan, M. J., and Selkoe, D. J. (2002) Naturally secreted oligomers of amyloid beta protein potently inhibit hippocampal long-term potentiation in vivo. Nature. 416, 535-539.

Webster, J. M., Zhang, R., Gambhir, S. S., Cheng, Z., and Syud, F. A. (2009) Engineered two-helix small proteins for molecular recognition. Chembiochem. 10, 1293-1296.

Wilson, D. M., and Binder, L. I. (1997) Free fatty acids stimulate the polymerization of tau and amyloid beta peptides. In vitro evidence for a common effector of pathogenesis in Alzheimer's disease. Am J Pathol. 150, 2181-2195.

Zheng, J., Liu, C., Sawaya, M. R., Vadla, B., Khan, S., Woods, R. J., Eisenberg, D., Goux, W. J., and Nowick, J. S. (2011) Macrocyclic β-Sheet Peptides That Inhibit the Aggregation of a Tau-Protein-Derived Hexapeptide. J. Am. Chem. Soc. 133, 3144-3157.

\* cited by examiner

5'-Phosphorylation of primers 2,3,5,6 and 7 followed by heat inactivation
Then Add primers 1 and 4, anneal and ligate

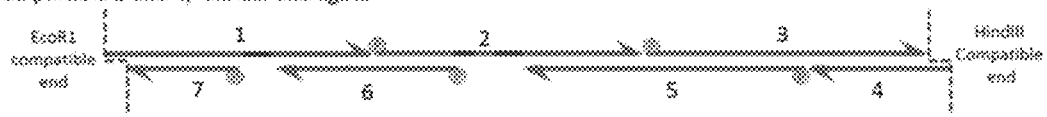

Gel extraction of 214 bp desired product (product has 2 single stranded gaps)

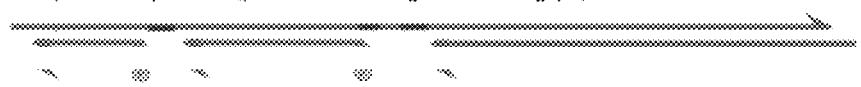

5'-Phosphorylation (NO heat inactivation) followed by PCR clean up kit

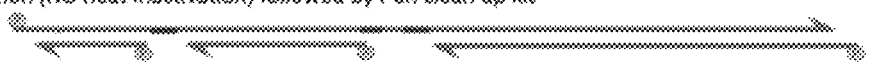

Ligation Directly into T7 vector Arms (this product still retains the 2 single stranded gaps.

Include in T7 packaging reaction to create a library:

FIG. 1

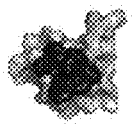
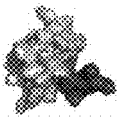
FIG. 3A-B

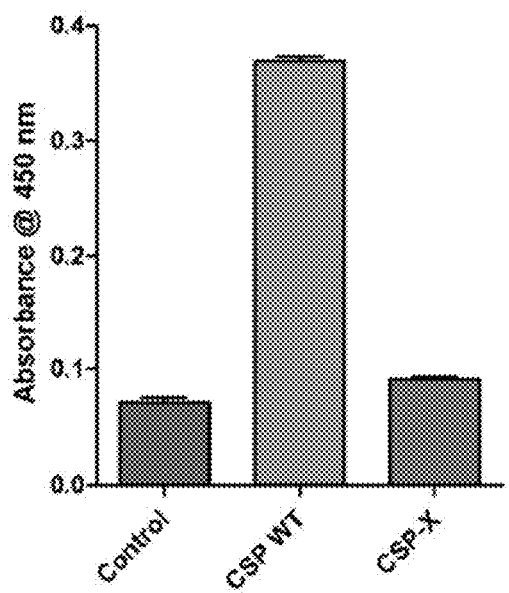 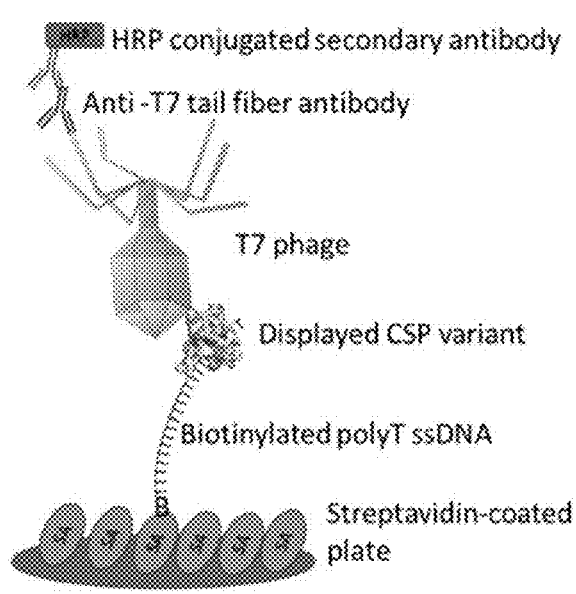
A                                             B
FIG. 4A-B

FIG. 6A-C

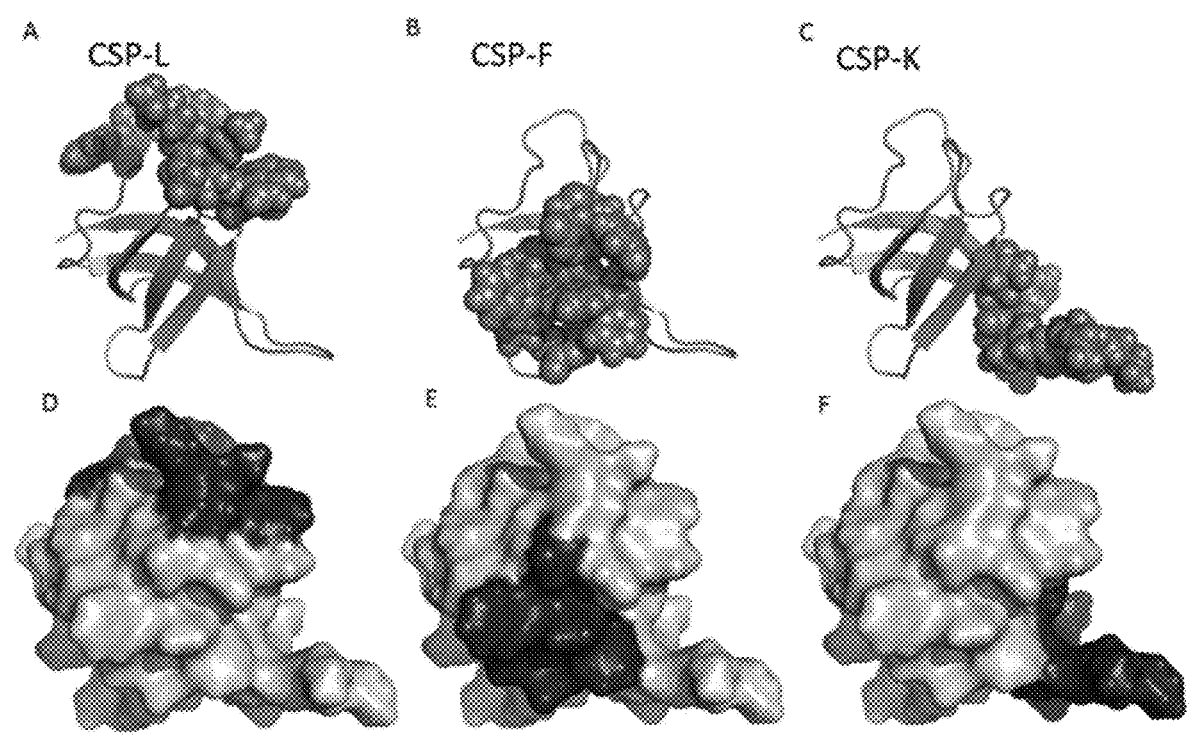
FIG. 8A-F

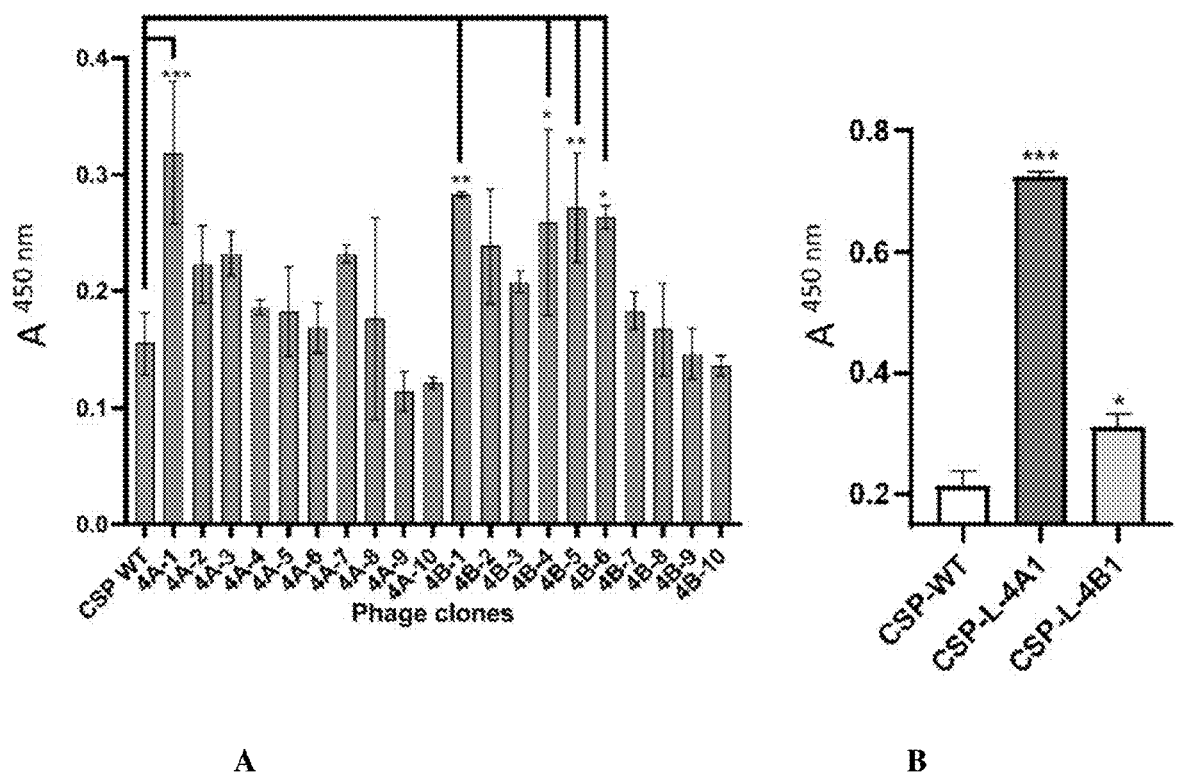
FIG. 9A-B

Data for rational design of CSP-derived proteins that bind tau fibrils.

..EIQEGKKGPQAA..

..EIQVQIVYKGPGSKYVIQVQAA..
..EIQGVQIVYKGPGSKYVIQVGQAA..

| His6-$^{Tm}$CSP(1-51)-linker-PHF6-turn-PHF6-linker-$^{Tm}$CSP(58-66) | | |
|---|---|---|
| PHF6 orientations | β-turns (type) | Linkers |
| -VQIVYK----KYVIQV- | GPSG (I) | none |
| -KYVIQV----VQIVYK- | GPGS (II) | G |
| | GGGG (II') | GA |

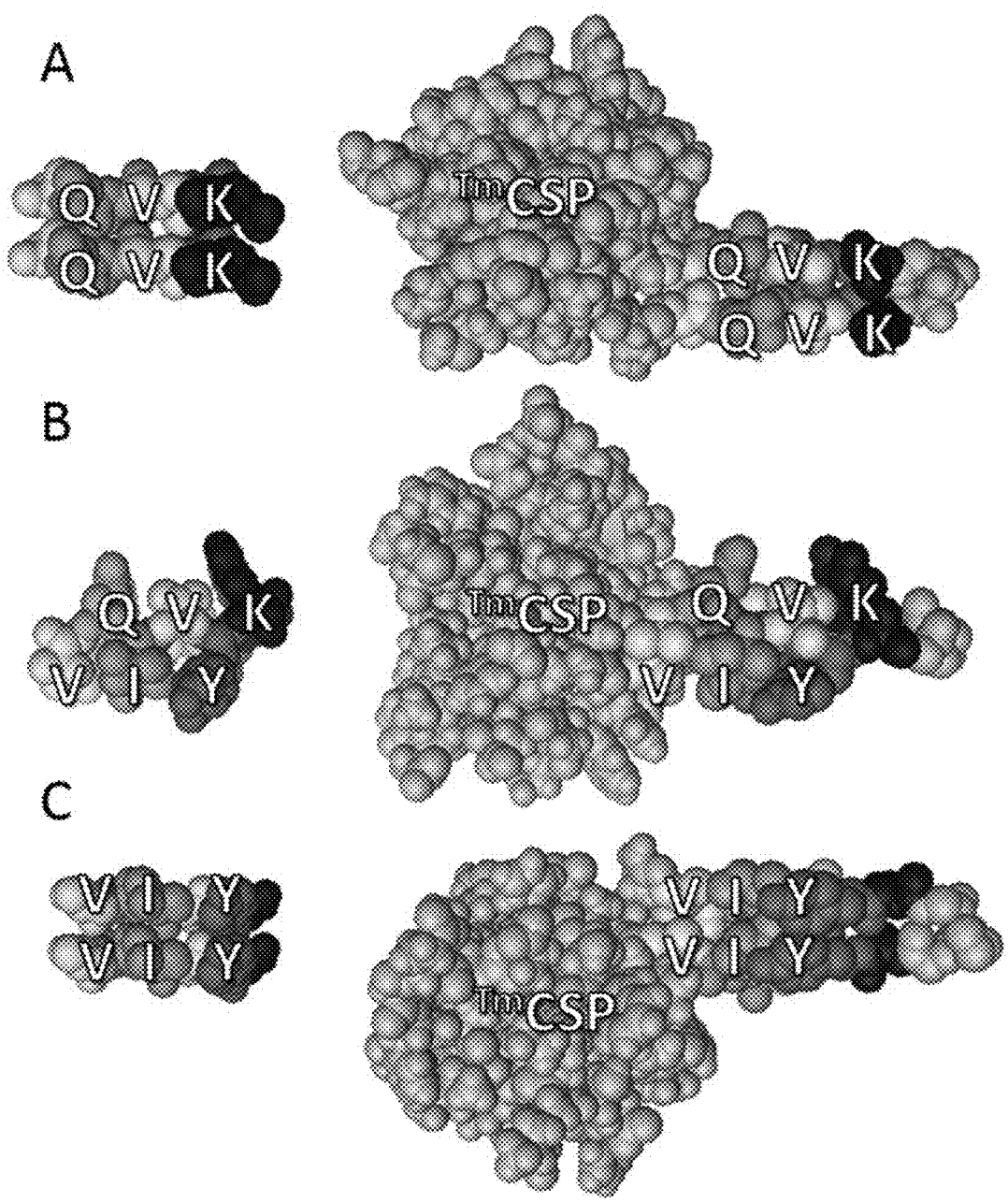
FIG. 16A-C

COLD-SHOCK PROTEIN SCAFFOLD FOR ENGINEERING NON-ANTIBODY BINDING PROTEINS

CROSS-REFERENCE TO RELATED APPLICATIONS

This application claims benefit of U.S. Provisional Application No. 63/199,885, filed Jan. 29, 2021, incorporated herein by reference in its entirety.

REFERENCE TO SEQUENCE LISTING

A Sequence Listing conforming to the rules of WIPO Standard ST.25 is hereby incorporated by reference. Said Sequence Listing has been filed as an electronic document via the USPTO patent electronic filing system in ASCII formatted text. The electronic document, created on Feb. 26, 2025, is entitled "11001-139US1 ST25", and is 29,099 bytes in size.

BACKGROUND

In recent years, antibodies have been a primary focus of biotechnological innovation for therapeutic uses and other diagnostic purposes. Their high specificity to targets and relatively inexpensive production means presents numerous opportunities for clinical applications. However, there are many instances where antibody related technologies are not ideal. For example, targeting of epitopes within the intracellular fluid of cells presents difficulties in many antibody models. The relatively large size of the peptide chain as well as the disulfide linkages generally restrict access to targets directly within the cytoplasm. While a few antibodies do provide some intracellular uses, such as those disclosed in U.S. Pat. No. 9,388,244, these technologies are typically restricted to lysosomal or endosomal compartments rather than targeting molecules directly within the cytoplasm itself. Other antibody related technologies have been proposed, such as cysteine-less single-chain antibody fragments, however the success rate in their development is often low. Furthermore, their use as effective diagnostic tools, such as biosensors, runs into difficulties involving stability due to the relatively short shelf-life which results in rapid degradation of the antibodies-based molecules.

Protein scaffolds are an alternate strategy to overcome many of these problems. Protein scaffolds, such as the Affibody® polypeptides derived from staphylococcal protein A (SpA) (U.S. Pat. No. 10,556,933), have achieved notable success in recent decades. These polypeptide scaffolds offer an improvement over antibodies for certain diagnostic and therapeutical purposes. The short peptide chains may be quickly cleared by renal secretion and offer added potential for sensing and imaging applications. Moreover, these molecules may be engineered to incorporate variable affinity to a binding agent for various therapeutical purposes. Presently, there are still ongoing issues limiting widespread usage of protein scaffolds in clinical and research applications which have been described in the literature (Vazquez-Lombardi et al. (2015)). Many of these scaffolds are derived from proteins without a human analog, thereby hindering the reduction of immunogenicity. In addition, a large number of these scaffolds are not sufficiently stable for a number of potential applications. Thus, novel protein scaffold variants with increased stability and diversity are needed to address these impediments.

SUMMARY

Disclosed herein is a recombinant binding protein scaffold comprising a polypeptide that is 75% or more identical to a naturally occurring cold-shock protein or cold shock domain-containing protein, and further wherein the cold-shock protein or cold shock domain-containing protein comprises a non-naturally occurring binding domain. The polypeptide may be based on the cold shock protein or cold shock domain from various organisms, including various plants and animals. Some embodiments of the present disclosure include cold shock proteins or cold shock domains derived from thermophile or hyperthermophile microorganisms, such as those displayed by the hyperthermophilic bacteria *Thermotoga maritima*.

Also disclosed herein are chimeric polypeptides comprising residues from two or more origins. These chimeric polypeptide scaffolds may include, for example, peptide sequences from a human cold shock protein or cold shock domain and residues from a microorganism. In certain aspects, the chimeric polypeptides include two or more mutations in a human cold shock domain.

Disclosed herein are conjugates and fusion proteins comprising the recombinant binding protein. In various instances, the conjugate or fusion protein comprises a moiety for targeted delivery of the recombinant protein scaffold. Also provided for are moieties comprising a drug, toxin, or nucleic acids. The present disclosure provides a method of binding a protein or peptide target with an analyte comprising a cold shock protein or cold shock domain, either alone, or as a conjugate or fusion protein.

Further disclosed herein is a polypeptide display library. The polypeptide display library can be used to screen and select molecules with a desired binding affinity to a target ligand. In some instances, the polypeptide display library is displayed on the surface of a ribosome, bacteriophage, virus, bacteria, or yeast. The polypeptide library may include a population of proteins containing mutations introduced by random mutagenesis, targeted mutagenesis, and/or rational design mutagenesis. Included herein are methods of obtaining a recombinant protein scaffold that binds to a desired target comprising (a) contacting a target ligand with the polypeptide display library under conditions that allow a scaffold:target ligand complex to form, and (b) obtaining from the complex, the scaffold that binds the target ligand.

BRIEF DESCRIPTION OF FIGURES

The accompanying drawings, which are incorporated in and constitute a part of this specification, illustrate certain examples of the present disclosure and together with the description, serve to explain, without limitation, the principles of the disclosure. Like numbers represent the same elements throughout the figures.

FIG. 1 depicts a representation of a strategy to synthesize $^{Tm}$CSP degenerate codon inserts compatible with T7 phage display.

FIG. 3A-B depicts the amino acid sequence of $^{Tm}$CSP-WT in comparison with the translation products of 21 unique clones sequenced from random isolated phage plaques from the $^{Tm}$CSP-L-VNK library. FIG. 3A shows sequences, which are SEQ ID NOS: 8-28, consecutively. FIG. 3B shows CSP molecules with the sites of amino acid randomization.

FIG. 4A-B depicts ELISA of $^{Tm}$CSP-displayed on phage binding to single strand polyT-DNA coated wells. A: raw data of ELISA signal. Control indicates T7 phage without the display of CSP. CSP-X indicates T7 phage displaying a variant of $^{Tm}$CSP with four mutations that reduce ssDNA binding (error bars reflect range, n=2). B: graphical representation of the ELISA format.

FIG. 8A-F depict various structural views (A-F) of *Thermotoga maritima* CSP with location of the three sets of eight amino acid sidechains designated for targeted randomization.

FIG. 9A-B depicts Screening of the CSP-L library against the microtubule associated protein tau (MAPT, Tau). A demonstrates that three rounds of enrichment by biopanning for affinity to Tau protein resulted in many clones with variable affinity for Tau protein by ELISA. B demonstrates that two of these clones selected for further assessment in a repeat experiment to confirm tau binding, suggesting higher affinity to tau than the CSP-WT control phage.

FIG. 10A-B depicts the tertiary structure of CSP-PHF6 rationally designed constructs. A shows the CSP WT protein. B shows where engineered regions of constructs fits into the CSP structure (shown in the dashed boxes). Sequences depicted are SEQ ID NOS: 37-39.

FIG. 11 depicts a table describing the modular design for a series of CSP-PHF6 constructs. The exposed β-turn and part of antiparallel β-sheets 4 and 5 was engineered to create anti-parallel β-sheets mimicking the stacked PHF6 region of tau found in tau fibrils. There are many options with two different PHF6 orientations, three different types of β-turns as well as the absence of presence of linker amino acids between the engineered region and the native region. Shown are SEQ ID NOS: 40-44.

FIG. 16A-C depicts Space filling models of the parallel n-sheet arrangement of PHF6 peptides (left) and of a proposed $^{Tm}$CSP-PHF62 protein with an antiparallel mimetic. A. View from the QVK face of the β-sheet. B. View rotated 90° about the X-axis showing the side view of the β-sheet. C. View from the VIY face of the β-sheet.

DETAILED DESCRIPTION

Definitions

Figure 2:
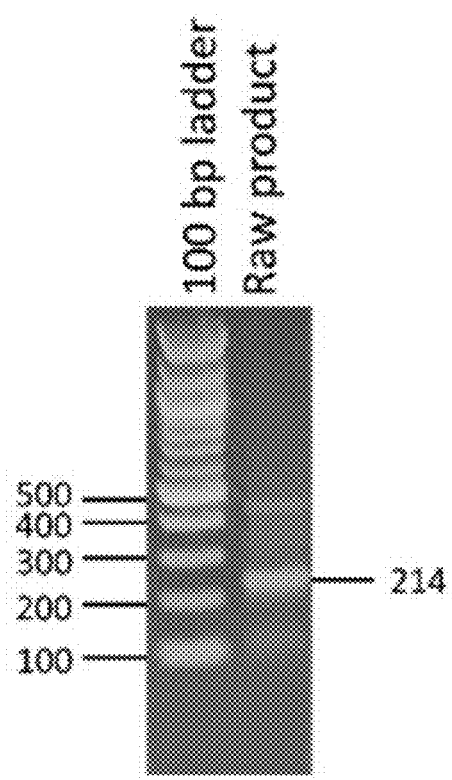
FIG. 2 shows the purity of the raw 214 bp insert, which was subsequently gel purified and used for insertion into the vector arms of T7 according to Example 1.
Figure 5:
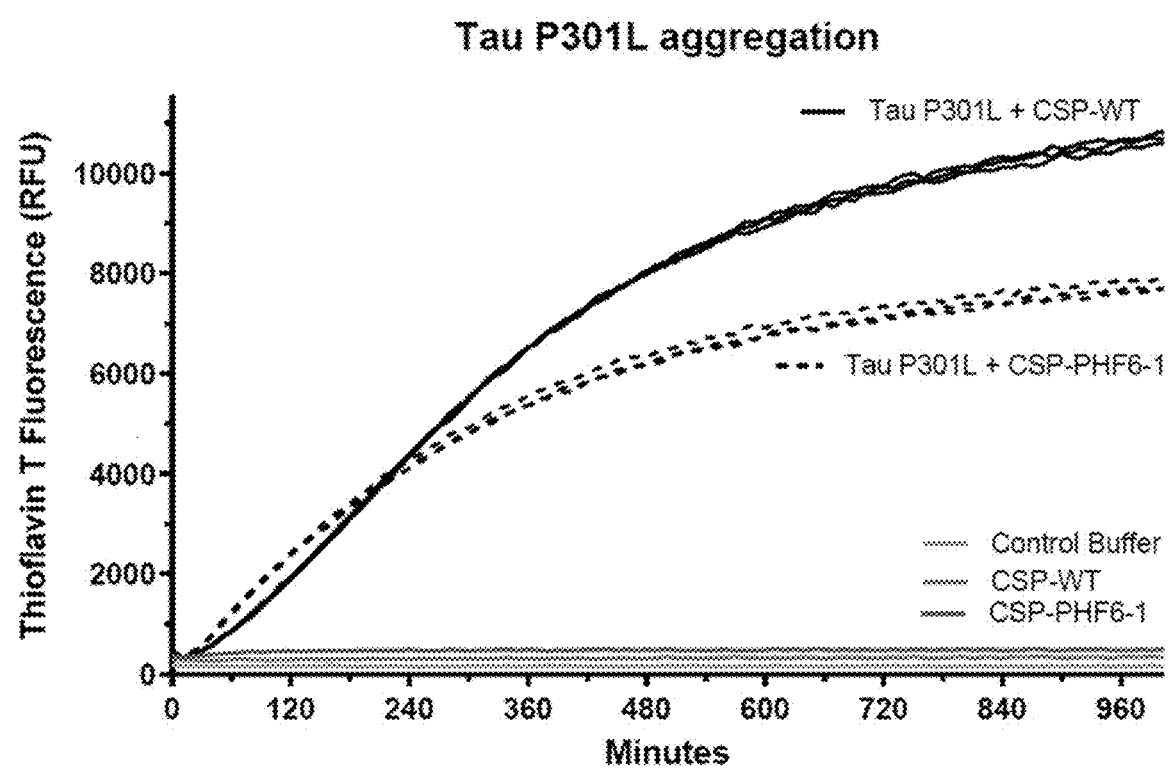
FIG. 5 depicts Thioflavin T fluorescence assay for Tau P301L protein in vitro aggregation in the presence of heparin and in the presence of either CSP-WT (black solid lines) or CSP-PHF6-1 (black dashed lines). Aggregation was monitored over the course of 16 hours. Control samples were carried out in the absence of Tau P301L demonstrate that CSP constructs alone did not aggregate (gray lines).
Figure 6:
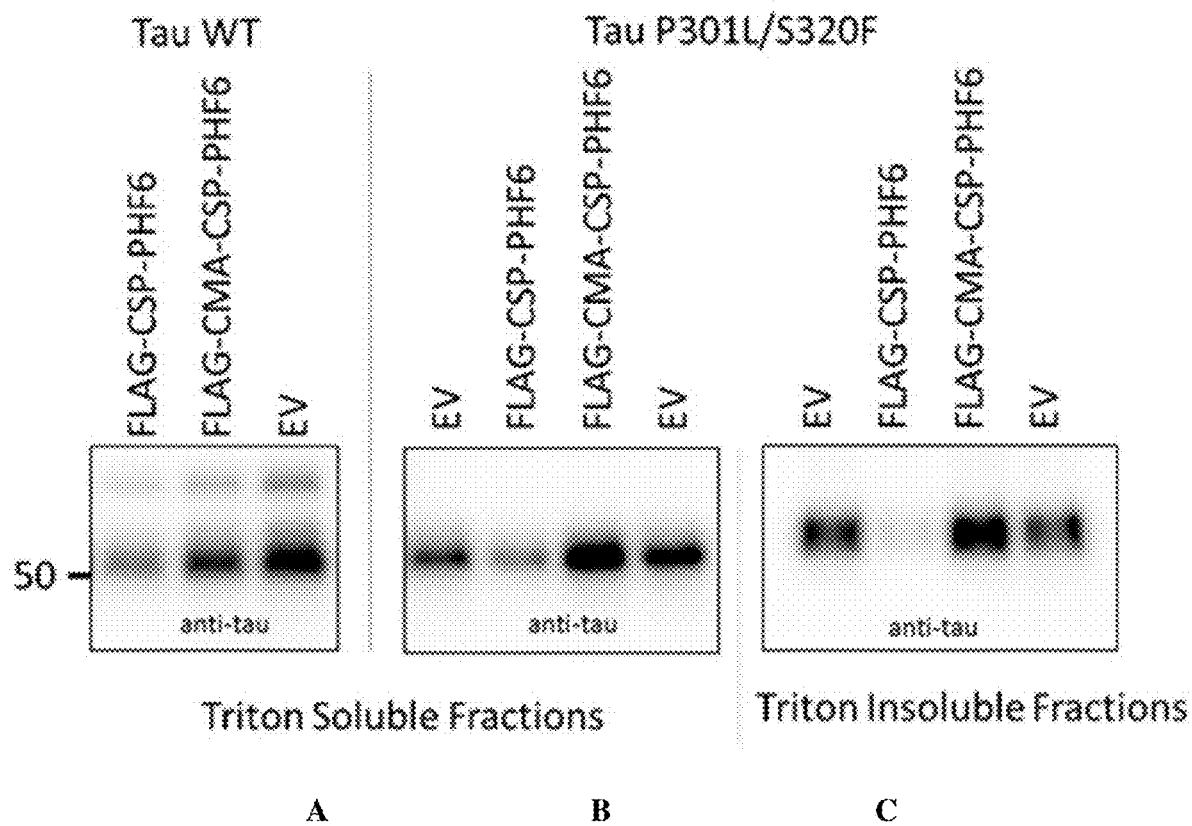
FIG. 6A-C depicts western blots comparing soluble and insoluble tau accumulation in lysates from HEK293T cells cotransfected with a tau expressing plasmid and either an empty vector plasmid (EV), a CSP-PHF6 expressing plasmid or a. CSP-PHF6 variant containing an additional engineered autophagic degron sequence (CMA). A shows Tau wildtype, B and C show Tau P301L/S320F.

In this specification and in the claims which follow, reference will be made to a number of terms which shall be defined to have the following meanings:

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular protein is disclosed and discussed and a number of modifications that can be made to the protein are discussed, specifically contemplated is each and every combination and permutation of the protein and the modifications that are possible unless specifically indicated to the contrary. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

As used in the specification and claims, the singular form "a", "an" and "the" include plural references unless the context clearly dictates otherwise.

"Comprising" refers to compounds, compositions and methods including the recited elements, but does not exclude others. "Consisting essentially of," when used to define compounds, compositions or methods, shall mean excluding other elements that would materially affect the basic and novel characteristics of the claimed technology. "Consisting of," shall mean excluding any element, step, or ingredient not specified in the claim. Embodiments defined by each of these transition terms are within the scope of this technology.

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having a disease or disorder. Subjects may be human, but also include other mammals, particularly those mammals useful as laboratory models for human disease, e.g. mouse, rat, etc.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

As used herein, "amino acid" refers to a compound containing both amino (—NH2) and carboxyl (—COOH) groups generally separated by one carbon atom. The central carbon atom may contain a substituent which can be either charged, ionisable, hydrophilic or hydrophobic. Any of 22 basic building blocks of proteins having the formula NH2-CHR—COOH, where R is different for each specific amino acid, and the stereochemistry is in the 'L' configuration. Additionally, the term "amino acid" can optionally include those with an unnatural 'D' stereochemistry and modified forms of the 'D' and 'L' amino acids.

As used herein, the terms "polypeptide," "peptide," or "protein" generally refer to a polymer of amino acid residues. As used herein, the term also applies to amino acid polymers in which one or more amino acids are chemical analogs or modified derivatives of corresponding naturally-occurring amino acids. The term "protein", as generally used herein, refers to a polymer of amino acids linked to each other by peptide bonds to form a polypeptide for which the chain length is sufficient to produce tertiary and/or quaternary structure. The term "protein" excludes small peptides by definition, the small peptides lacking the requisite higher-order structure necessary to be considered a protein.

Different modifications of, and/or additions to, the polypeptides constituting the population according to the invention may be performed in order to tailor the polypeptides to the specific use intended. Such modifications and additions are described in more detail below, and may comprise additional amino acids comprised in the same polypeptide chain, or labels and/or therapeutic agents that are chemically conjugated or otherwise bound to the polypeptides constituting the population. In some embodiments additional amino acid residues on the C-terminal end may be preferred. These additional amino acid residues may play a role in the binding of the polypeptide, but may equally well serve other purposes, related for example to one or more of the production, purification, stabilization, coupling or detection of the polypeptide. Such additional amino acid residues may comprise one or more amino acid residues added for purposes of chemical coupling. An example of this is the addition of a cysteine residue at the very first or very last position in the polypeptide chain, i.e. at the N- or C-terminus. A cysteine residue to be used for chemical coupling may also be introduced by replacement of another amino acid on the surface of the protein domain, preferably on a portion of the surface that is not involved in target binding. Such additional amino acid residues may also comprise a "tag" for purification or detection of the polypeptide, such as a hexahistidyl ($His_6$) tag, or a "myc" tag or a "FLAG" tag for interaction with antibodies specific to the tag. The skilled person is aware of other alternatives.

The "additional amino acid residues" discussed above may also constitute one or more polypeptide domain(s) with any desired function, such as another binding function, or an enzymatic function, or a metal ion chelating function, or a fluorescent function, or mixtures thereof.

The "percentage of sequences identity" is determined by comparing two optimally aligned sequences over a comparison window, wherein the portion of the sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% identity over a specified region), when compared and aligned for maximum correspondence over a comparison window, or designated region as measured using one of the following sequence comparison algorithms or by manual alignment and visual inspection. These definitions also refer to the complement of a test sequence. Optionally, the identity exists over a region that is at least about 50 nucleotides in length, or more typically over a region that is 100 to 500 or 1000 or more nucleotides in length.

The terms "similarity" or "percent similarity" in the context of two or more polypeptide sequences, refer to two or more sequences or subsequences that have a specified percentage of amino acid residues that are either the same or similar as defined by a conservative amino acid substitutions (e.g., 60% similarity, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences are "substantially similar" to each other if they are at least 20%, at least 25%, at least 30%, at least 35%, at least 40%, at least 45%, at least 50%, or at least 55% similar to each other. Optionally, this similarly exists over a region that is at least about 25 amino acids in length (e.g., at least 30, at least 35, at least 40, at least 45, at least 50, at least 55, at least 60, at least 65, at least 70, at least 75), or more typically over a region that is at least about 100 to 500 or 1000 or more amino acids in length. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are commonly used, or alternative parameters can be designated. The sequence comparison algorithm then calculates the percent sequence identities or similarities for the test sequences relative to the reference sequence, based on the program parameters.

Expressions like "binding affinity for a target", "binding to a target" and the like refer to a property of a polypeptide which may be directly measured through the determination of the affinity constants i.e. the amount of polypeptide that associates and dissociates at a given antigen concentration. Different methods can be used to characterize the molecular interaction, such as, but not limited to, competition analysis, equilibrium analysis and microcalorimetric analysis, and real-time interaction analysis based on surface plasmon resonance interaction (for example using a BIACORE instrument). These methods are well-known to the skilled person and are described, for example, in Neri D et al (1996) Tibtech 14:465-470 and Jansson M et al (1997) J Biol Chem 272:8189-8197.

The term "panning" or "biopanning" as used herein refers to the process of an affinity selection technique which selects for peptides or polypeptides, (collectively also referred to as "binders") that bind to a predetermined (given) target. The process of panning involves four major steps for selection of binders. The first step is to provide a display library. In a specific embodiment the display library is a composition comprising a population of ternary complexes as described in any of the embodiments disclosed herein. The second step is the capturing step. It involves contacting the display library with the desired target. In a specific embodiment the target is immobilized. By way of specific binding interaction only specific displayed binding domains presented by any of the peptides, polypeptides, and chimeric polypeptides are bound to the target. The third step is a separation step, subsequent to the capturing step, to separate the bound members of the display library from unbound members by way of removing the unbound members. In a specific embodiment the separation is performed as a washing step wherein a mixture comprising immobilized target with bound members of the display library is washed, thereby removing unbound members. As a result of the separation step, target-bound members of the display library are retained. The fourth step is a recovery step where the bound members or components thereof are recovered and/or enriched and/or purified, for further processing and/or characterization.

As used herein, "cold shock protein" is a collective designation for proteins which are expressed in organisms, particularly in microorganisms, when they are exposed to the cold shock by downshift of growth temperatures. For example, when an incubation temperature of *Escherichia coli* is reduced from 37° C. to 15° C., cold shock protein, which is called CspA, is transiently expressed at a high level. It is known that *Escherichia coli* has eight different proteins, CspB to CspI, which have high amino acid sequence identity to CspA. Of these proteins, CspB, CspG and CspI are the cold shock proteins. Further, cold shock proteins exist in various microorganisms such as *Bacillus subtilis* (CspB), *Bacillus caldolyticus* (CspB), *Thermotoga maritima* (CspB, CspL) and *Lactobacillus plantarum* (CspL). In particular, cold-shock proteins derived from *Thermotoga maritima* ($^{Tm}$CSP) are known to exhibit high thermostability (Phadtare et al., Genes to Cells, 8:801-10, 2003). The cold-shock protein or cold shock domain containing protein used as the basis of the protein scaffold may be prepared synthetically through recombinant expression (such as solid phase peptide synthesis) or may be isolated from a microorganism. In some embodiments, the cold-shock protein has a length of less than 100 amino acids (e.g. less than 99 amino acids, less than 98 amino acids, less than 97 amino acids, less than 96 amino acids, less than 95 amino acids, less than 94 amino acids, less than 93 amino acids, less than 92 amino acids, less than 91 amino acids, less than 90 amino acids, less than 89 amino acids, less than 88 amino acids, less than 87 amino acids, less than 86 amino acids, less than 85 amino acids, less than 84 amino acids, less than 83 amino acids, less than 82 amino acids, less than 81 amino acids, less than 80 amino acids, less than 79 amino acids, less than 78 amino acids, less than 77 amino acids, less than 76 amino acids, less than 75 amino acids, less than 74 amino acids, less than 73 amino acids, less than 72 amino acids, less than 71 amino acids, less than 70 amino acids, less than 69 amino acids, less than 68 amino acids, less than 67 amino acids, less than 66 amino acids, less than 65 amino acids, less than 64 amino acids, less than 63 amino acids, less than 62 amino acids, less than 61 amino acids, or less than 60 amino acids). References to mutations of a cold shock protein or cold shock domain containing protein refer to mutations made within the amino acid residues of the cold shock domain of said protein.

As used herein, the term "protein scaffold" or "scaffold" refers to a conformationally constant, stably folding polypeptide entity capable of displaying a multitude of amino-acid sequences as a separate (i.e. as a non-scaffold) segment or domain in a localized surface region. A scaffold is particularly useful for discovery and engineering of such separate domains capable of interacting with and/or specifically binding to a predetermined target such as an antigen or an antigen epitope, an active site of a bioactive molecule, etc. Desirable physical properties of a protein scaffold include high thermal stability and reversibility of thermal folding and unfolding.

The term "library" refers to a mixture of heterogeneous polypeptides or nucleic acid molecules, also referred to as "population" of polypeptides or nucleic acid molecules. The library is composed of a plurality of "species", each of which has a substantially unique amino acid or nucleotide sequence. Sequence differences between library species are responsible for the diversity present in the library or population. In the present disclosure the library may take the form of a simple mixture of polypeptides or nucleic acid molecules or may be present in the form of biological complexes in a biochemical environment for translation or combined transcription and translation. In some aspects, the library may contain a diversity of at least $1\times10^6$, at least $2\times10^6$, at least $3\times10^6$, at least $4\times10^6$, at least $5\times10^6$, at least $6\times10^6$, at least $7\times10^6$, at least $8\times10^6$, at least $9\times10^6$, $1\times10^7$, at least $2\times10^7$, at least $3\times10^7$, at least $4\times10^7$, at least $5\times10^7$, at least $6\times10^7$, at least $7\times10^7$, at least $8\times10^7$, at least $9\times10^7$, $1\times10^8$, $1\times10^8$, at least $2\times10^8$, at least $3\times10^8$, at least $4\times10^8$, at least $5\times10^8$, at least $6\times10^8$, at least $7\times10^8$, at least $8\times10^8$, at least $9\times10^8$, $1\times10^9$, $1\times10^9$, at least $2\times10^9$, at least $3\times10^9$, at least $4\times10^9$, at least $5\times10^9$, at least $6\times10^9$, at least $7\times10^9$, at least $8\times10^9$, at least $9\times10^9$, $1\times10^{10}$, $1\times10^{10}$, at least $2\times10^{10}$, at least $3\times10^{10}$, at least $4\times10^{10}$, at least $5\times10^{10}$, at least $6\times10^{10}$, at least $7\times10^{10}$, at least $8\times10^{10}$, at least $9\times10^{10}$, or at least $1\times10^{10}$.

As used herein, "analyte" generally refers to a substance to be detected. In some embodiments, analytes are those that are sometimes found in a sample in low concentration, such as at concentrations below a detection limit of a measurement system. Some analytes are typically present in a sample at high concentrations, but may be present in a particular sample to be tested at low concentration due to a particular disorder, due to the phase of a disorder, or due to sample processing. For example, an analyte may be present in a sample at low concentration at initial stages of a disease or disorder or following a peak stage of a disease or disorder.

Analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles, and metabolites of or antibodies to any of the above substances. Additional analytes may be included for purposes of biological or environmental substances of interest.

Recombinant Binding Protein Scaffolds

Disclosed herein are recombinant binding protein scaffolds, wherein said scaffolds comprise a polypeptide that is 60% or more identical to a naturally occurring cold-shock protein or cold shock domain-containing protein, and further wherein the cold-shock protein or cold shock domain-containing protein comprises a non-naturally occurring binding domain. In some aspects the scaffold comprises a polypeptide that is 60% or more identical to the naturally occurring cold-shock protein or cold shock domain containing protein, such as, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, or 95% or more.

The cold-shock proteins or cold-shock domain-containing proteins which forms the basis of the recombinant protein scaffold includes any naturally occurring cold-shock proteins or cold-shock domain-containing proteins, such as those discussed in Heinemann et al., Cancers 13(2):190 (2021) which is incorporated by reference in its entirety. In some aspects, the cold-shock protein is derived from a microorganism. For example, the cold-shock protein or cold-shock domain containing protein may include a protein derived from or produced by a thermophile or hyperthermophile microorganism. In certain aspects, the microorganism and protein are *Escherichia coli* (CspA, CspB, CspC, CspD, CspE, CspF, CspG, CspH, CspI), *Bacillus subtilis* (CspB, CspC, CspD), *Bacillus caldolyticus* (CspB), *Thermotoga maritima* (CspB, CspL) and/or *Lactobacillus plantarum* (CspL). In various aspects, the protein scaffold does not include a cysteine residue or disulfide bond.

In particular embodiments, the cold-shock protein or cold-shock domain containing protein is derived from the extremophile *Thermotoga maritima*. For example, the recombinant protein scaffold may comprise at least 70% sequence identity to SEQ ID NO: 1, such as at least 71% sequence identity to SEQ ID NO: 1, at least 71% sequence identity to SEQ ID NO: 1, at least 73% sequence identity to SEQ ID NO: 1, at least 74% sequence identity to SEQ ID NO: 1, at least 75% sequence identity to SEQ ID NO: 1, at least 76% sequence identity to SEQ ID NO: 1, at least 77% sequence identity to SEQ ID NO: 1, at least 78% sequence identity to SEQ ID NO: 1, at least 79% sequence identity to SEQ ID NO: 1, at least 80% sequence identity to SEQ ID NO: 1, at least 81% sequence identity to SEQ ID NO: 1, at least 82% sequence identity to SEQ ID NO: 1, at least 83% sequence identity to SEQ ID NO: 1, at least 84% sequence identity to SEQ ID NO: 1, at least 85% sequence identity to SEQ ID NO: 1, at least 86% sequence identity to SEQ ID NO: 1, at least 87% sequence identity to SEQ ID NO: 1, at least 88% sequence identity to SEQ ID NO: 1, at least 89% sequence identity to SEQ ID NO: 1, at least 90% sequence identity to SEQ ID NO: 1, at least 91% sequence identity to SEQ ID NO: 1, at least 92% sequence identity to SEQ ID NO: 1, at least 93% sequence identity to SEQ ID NO: 1, at least 94% sequence identity to SEQ ID NO: 1, at least 95% sequence identity to SEQ ID NO: 1, at least 96% sequence identity to SEQ ID NO: 1, or at least 97% sequence identity to SEQ ID NO: 1.

In other aspects, the cold-shock protein or cold-shock domain containing protein include cold shock proteins from complex organisms, such as proteins derived from an animal or plant. For example, the cold shock protein may be a human cold-shock protein or cold-shock domain containing protein, such as YB-1, DbpC, DbpA (any isoform), CAR-HSP1, PIPPin, UNR (any isoform), LIN28A, or LIN28B (SEQ ID NO: 6) as discussed by Lindquist et al., Cell Commun. Signal 16:63 (2018).

Also included are recombinant binding protein scaffolds comprising a chimeric polypeptide. A chimeric polypeptide refers to a polypeptide whose amino acid sequence represents a fusion product of subsequences of the amino acid sequences from at least two distinct origins. Chimeric mutations may be included to improve certain properties or characteristics of the recombinant protein scaffold, such as improving stability of the polypeptide or increasing or decreasing affinity to a target. A chimeric protein typically is not produced by direct manipulation of amino acid sequences, but, rather, is expressed from a "chimeric" nucleic acid molecule that encodes the chimeric amino acid sequence. Thus, the chimeric polypeptide may be created through the joining in-frame of two or more coding nucleic acid sequences which originally code for separate polypeptides or polypeptide domains. In a specific embodiment, translation of the fused coding sequence results in a single polypeptide with functional properties derived from each of the original polypeptides or polypeptide domains. In some embodiments, the chimeric polypeptide comprises amino acid sequences from a human cold-shock domain and another source. For example, the chimeric polypeptide may include a human cold shock domain having two or more mutations that resemble the protein from a microorganism. In some embodiments, the two or more (such as three or more, four or more, five or more, six or more, seven or more, eight or more, nine or more, or ten or more) mutations to the human cold shock domain containing protein are based on sequences found in *Thermotoga maritima* cold shock proteins. For example, the human cold shock domain Lin28B may include mutations based on the sequences found in $^{Tm}$CSP, such as C34V, M48I, P82V, T85E, E52D, R98K. These mutations in the Lin28B (SEQ ID NO: 6) domain approximate residues V5, 117, V45, E47, D20, and K63 of SEQ ID NO: 1, respectively.

In particular aspects, the chimeric polypeptide comprises mutations to a from a similarly structured cold shock protein domains. Cold shock proteins are considered similarly structured where at least 75% of the structure of the cold shock proteins have an average root-mean-square deviation (RMSD) from backbone atoms in secondary structure elements in at least one domain of a three dimensional structure of less than or equal to 3.0 Å (e.g. less than or equal to 2.9 Å, less than or equal to 2.8 Å, less than or equal to 2.7 Å, less than or equal to 2.6 Å, less than or equal to 2.5 Å, less than or equal to 2.4 Å, less than or equal to 2.3 Å, less than or equal to 2.2 Å, less than or equal to 2.1 Å, less than or equal to 2.0 Å, less than or equal to 1.9 Å, less than or equal to 1.8 Å, less than or equal to 1.7 Å, less than or equal to 1.6 Å, less than or equal to 1.5 Å, less than or equal to 1.4 Å, less than or equal to 1.3 Å, less than or equal to 1.2 Å, less than or equal to 1.1 Å, less than or equal to 1.0 Å, less than or equal to 0.9 Å, less than or equal to 0.8 Å, less than or equal to 0.7 Å, less than or equal to 0.6 Å, or less than or equal to 0.5 Å).

The present disclosure provides for recombinant binding protein scaffolds comprising a binding domain. In some embodiments, the binding domain refers to a region on the binding protein scaffold where the cold shock protein or cold shock domain displays affinity to a target molecule, such as a protein or peptide of interest. For example, the cold shock protein or cold shock domain may include one or more mutations resulting in a region having an increased affinity to a target molecule compared to the unmutated cold shock protein or cold shock domain. For example, the recombinant binding protein scaffold of the present disclosure may comprise a PHF6 sequence (SEQ ID NO: 31) or a PHF6* sequence (SEQ ID NO: 32), which are shown to bind tau aggregates (Ganguly et al. J. Phys. Chem. B., 119(13):4582-4593, 2015). Additionally provided herein are recombinant binding protein scaffolds comprising an RGD sequence, which are known to have an affinity to integrins (Ruoslahti, Annu. Rev. Cell Dev. Bio., 12:697-715, 1996). In other embodiments, the binding domain comprises a region on the cold shock protein or cold shock domain that naturally displays affinity to a desired target molecule.

In certain other aspects, the binding domain refers to a region on the binding protein scaffold where the cold shock protein or cold shock domain is coupled with a binding molecule. For example, the binding domain may include a region on the scaffold wherein the binding protein scaffold is covalently coupled with a binding molecule. The scaffold may comprise a means of detection, which includes binding moieties or labels within the polypeptide capable of external expression, including, for example, fluorescence, an enzyme, superparamagnetic particles, or radioactive labels. In some embodiments, the radioactive label comprises one or more of $^{11}$Carbon, $^{11}$Fluorine, $^{13}$Carbon, $^{15}$Nitrogen, $^{18}$Fluorine, $^{19}$Fluorine, $^{32}$Phosphate, $^{60}$Cobalt, $^{90}$Yttrium, $^{99}$Technetium, $^{103}$Palladium, $^{106}$Ruthenium, $^{111}$Indium, $^{117}$Lutetium, $^{125}$Iodine, $^{131}$Iodine, $^{137}$Cesium, $^{153}$Samarium, $^{186}$Rhenium, $^{188}$Rhenium, $^{192}$Iridium, $^{198}$Gold, $^{211}$Astatine, $^{212}$Bismuth, and/or $^{213}$Bismuth. In some aspects, the radioactive label comprises one or more of $^{67}$Copper, $^{67}$Gallium, $^{68}$Gallium, $^{111}$Indium, $^{113}$Indium, $^{123}$Iodine, $^{125}$Iodine, $^{131}$Iodine, $^{197}$Mercury, $^{203}$Mercury, $^{186}$Rhenium, $^{188}$Rhenium, $^{97}$Rubidium, $^{103}$Rubidium, $^{99}$Technetium, $^{201}$Thallium, $^{133}$Xenon, and/or $^{90}$Yttrium.

In general, the binding domain may be selected based on a structural or affinity characteristic of the protein scaffold. For example, when the cold shock protein comprises at least 75% (e.g. at least 80%, at least 85%, at least 90%, at least 95%, or 100%) sequence identity to SEQ ID NO: 1, the binding domain may comprise, for example, sidechains in loops between beta sheets 1 and 2 and between beta sheets 3 and 4. In some aspects where the cold shock protein comprises at least 75% sequence identity to SEQ ID NO: 1, the binding domain may comprise at least two amino acids in positions 10, 11, 12, 29, 30, 35, 36, and 37 of SEQ ID NO: 1. This region contains loops without any secondary structure, but is held in place by stable interactions between the 5-beta-sheet core of the protein, which is a randomization strategy similar to the variable complementarity determining regions (CDRs) found in antibodies. Some binding domains may be located in sidechains exposed on antiparallel beta sheets 1, 2, and 3. For example, the binding domain may comprise at least two amino acids in positions 6, 7, 9, 14, 15, 16, 24, and 26 of SEQ ID NO: 1, which allows targeting of different epitopes. Furthermore, the binding domain may comprise residues within sidechains in a beta-turn and part of antiparallel beta sheets 4 and 5. In some embodiments, the binding domain comprises at least two amino acids in positions 51, 52, 53, 54, 55, 56, 57, and 58 of SEQ ID NO: 1. Binding domains encompassing residues in this region may enable the targeting of various types of epitopes, including those that are less accessible to other regions.

In some aspects, modifications to the cold-shock protein or cold shock domain containing protein may be included such that cold-shock protein or cold shock domain containing protein does not bind to its natural target (single-stranded DNA) or binds with a reduced affinity. For example, when the cold-shock protein comprises a polypeptide sequence comprising at least 75% sequence identity to SEQ ID NO: 1 (e.g., at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, or at least 97%) modifications at one or more residues of Y14A, F16A, F26A, and/or H28Q may be may to reduce or eliminate binding affinity to its natural target (ss poly-T DNA). These modifications reducing or eliminating affinity to a natural target may be made alone or with subsequent mutations (e.g. at least one further modification, at least two further modifications, at least three further modifications, at least four further modifications, at least five further modifications, at least six further modifications, at least seven further modifications, at least eight further modifications, at least nine further modifications, or at least ten further modifications).

Additionally disclosed herein are conjugates and fusion proteins. Fusion proteins can comprise one or more recombinant binding scaffolds (e.g., 2 or more, 3 or more, 4 or more, 5 or more, or 6 or more). The two or more recombinant binding scaffolds may comprise two or more identical recombinant binding protein scaffolds or two or more different recombinant binding protein scaffolds.

Conjugates and Fusion Proteins

The recombinant binding protein scaffolds disclosed herein have utility on their own without conjugation and may be utilized without further modification. However, the conjugation of effector function, cytotoxic or imaging agents is yet another embodiment, as the added moieties also add functionality to the recombinant binding protein scaffolds. In some embodiments, the conjugate comprising the recombinant binding protein scaffold may sequester the target protein or peptide.

Recombinant binding protein scaffolds may be coupled or conjugated to one or more therapeutic cytotoxic or imaging moieties. In certain aspects of the present disclosure, the conjugate comprises a moiety which assists in targeted delivery. The moiety may comprise a detachable moiety. For example, the moiety may comprise a drug, toxin, nucleic acid, or other therapeutic agent for therapeutic delivery. In other embodiments, the moiety comprises a transduction domain or cell penetrating peptide capable of carrying proteins, peptides, nucleic acids, and nanoparticles through the cellular membrane. Various transduction domains and cell penetrating peptides are known in the art.

In some aspects, the recombinant binding protein scaffold may be used in a method of binding a protein or peptide target. The method generally includes providing a sample with the recombinant binding protein scaffold under suitable conditions to enable binding of the recombinant binding protein scaffold to the target protein or peptide target. Suitable conditions to enable binding of the protein scaffold to the target protein or peptide target are dependent on the specific protein scaffold and target protein or peptide and are known by skilled artisans without undue experimentation. Specific instances of some suitable conditions are demonstrated within the examples listed below.

The method may be employed for various types and locations of target proteins or peptides. In some aspects, the target protein or peptide comprises a target within a cell, such as a target within the cytoplasm of a cell. The method may be used to bind to specific targets in cells that are in vivo, in vitro, or ex vivo. For example, the cell may be within an organism, such as a microorganism, a plant, or a mammal (e.g., a human). In some embodiments, the above disclosed conjugate may be immobilized to form the basis of a diagnostic assay, such as an ELISA.

As used herein, "cytotoxic moiety" simply means a moiety that inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. As utilized herein, "imaging moiety" means a moiety which can be utilized to increase contrast between a tumor and the surrounding healthy tissue in a visualization technique (e.g., radiography, positron-emission tomography, magnetic resonance imaging, direct or indirect visual inspection.) Thus, suitable imaging moieties include microbubbles, radiography moieties (e.g, heavy metals and radiation emitting moieties), positron emitting moieties, magnetic resonance contrast moieties, and optically visible moieties (e.g., fluorescent or visible-spectrum dyes, visible particles, etc.). It will be appreciated by one of ordinary skill that some overlap exists between what is a therapeutic moiety and what is an imaging moiety. For example, microbubbles are useful for delivery of drugs, in addition to their imaging properties.

In general, therapeutic or imaging agents may be conjugated to the recombinant binding protein scaffolds by any suitable technique, with appropriate consideration of the need for pharmacokinetic stability and reduced overall toxicity to the patient. A therapeutic agent may be coupled either directly or indirectly (e.g. via a linker group). A direct reaction between an agent and a scaffold is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance a scaffold from an agent in order to avoid interference with binding capabilities. A linker group can also serve to increase the chemical reactivity of a substituent on a moiety or a scaffold, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the scaffold moiety) and succinimidyl linkers (which react with a primary amine on the scaffold moiety). It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, therapeutic or imaging moieties may be coupled to the scaffold moiety through an oxidized carbohydrate group at a glycosylation site, as described in U.S. Pat. Nos. 5,057,313 and 5,156,840. Yet another alternative method of coupling the recombinant binding protein scaffolds to the cytotoxic or imaging moiety is by the use of a non-covalent binding pair, such as streptavidin/biotin, or avidin/biotin. In these embodiments, one member of the pair is covalently coupled to the scaffold moiety and the other member of the binding pair is covalently coupled to the cytotoxic or imaging moiety.

Imaging conjugates may comprise any of a variety of agents, e.g. contrast agents such as microbubbles, fluorophores, radio-agents, and the like as known in the art.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Examples of such compositions which may be utilized for x-ray radiography are described in U.S. Pat. No. 5,709,846, incorporated fully herein by reference. Such moieties may be conjugated to the recombinant binding protein scaffold moiety through an acceptable chemical linker or chelation carrier.

Preferred magnetic resonance contrast moieties include chelates of chromium(III), manganese(II), iron(II), nickel (II), copper(II), praseodymium(III), neodymium(III), samarium(III) and ytterbium(III) ion. Because of their very strong magnetic moment, the gadolinium(III), terbium(III), dysprosium(III), holmium(III), erbium(III), and iron(III) ions are especially preferred. Examples of such chelates, suitable for magnetic resonance spin imaging, are described in U.S. Pat. No. 5,733,522, incorporated fully herein by reference. Nuclear spin contrast chelates may be conjugated to the recombinant binding protein scaffold moieties through a suitable chemical linker.

Optically visible moieties for use as imaging moieties include fluorescent dyes, or visible-spectrum dyes, visible particles, and other visible labeling moieties. Fluorescent dyes such as fluorescein, coumarin, rhodamine, Texas red, and cyanine dyes such as indocyanine green, are useful when sufficient excitation energy can be provided to the site to be inspected visually. Endoscopic visualization procedures may be more compatible with the use of such labels. For many procedures where imaging agents are useful, such as during an operation to resect a brain tumor, visible spectrum dyes are preferred. Acceptable dyes include FDA-approved food dyes and colors, which are non-toxic, although pharmaceutically acceptable dyes which have been approved for internal administration are preferred. Alternatively, visible particles, such as colloidal gold particles or latex particles, may be coupled to the recombinant binding protein scaffold moiety via a suitable chemical linker.

In some embodiments, methods are utilized for imaging use in vivo, e.g., to locate or identify sites where tumor cells are present. The phrase "in vivo imaging" as used herein refers to methods of detecting the presence of an recombinant binding protein scaffold in whole, live mammal. In these embodiments, a detectably-labeled moiety, e.g., an recombinant binding protein scaffold, which is specific for a cancer marker, is administered to an individual (e.g., by injection), and labeled cells are located using standard imaging techniques, including, but not limited to, Positron emission tomography (PET), Magnetic resonance imaging (MRI), Computed tomography (CT), Optical Imaging (OI), Photoacoustic Imaging (PI), and Ultrasound Imaging (US), and the like. The conjugate comprising the scaffold may be labeled with a radionuclide or a microbubble for this purpose. Optically detectable proteins such as fluorescent and luciferases-conjugated proteins may also be detected by in vivo imaging. In vivo imaging of fluorescent proteins in live animals is described in, e.g., Hoffman, Cell Death and Differentiation 2002, 9:786-789.

In general, any conventional method for visualizing diagnostic imaging can be utilized in accordance with this invention, using clinical imaging instruments. For diagnostic in vivo imaging, the type of detection instrument available is a factor in selecting a given radionuclide. A radionuclide chosen must have a type of decay that is detectable by a given type of instrument. Another important factor in selecting a radionuclide for in vivo diagnosis is that its half-life be long enough that it is still detectable at the time of maximum uptake by the target tissue, but short enough that deleterious radiation of the host is minimized.

The detectably labeled recombinant binding protein scaffold is used in conjunction with imaging techniques, in order to analyze the expression of the target. In one embodiment, the imaging method is one of PET or SPECT, which are imaging techniques in which a radionuclide is synthetically or locally administered to a patient. The subsequent uptake of the radiotracer is measured over time and used to obtain information about the targeted tissue. Because of the high-energy (γ-ray) emissions of the specific isotopes employed and the sensitivity and sophistication of the instruments used to detect them, the two-dimensional distribution of radioactivity may be inferred from outside of the body. Among the most commonly used positron-emitting nuclides in PET are included $^{11}$C, $^{13}$N, $^{15}$O, and $^{18}$F. Isotopes that decay by electron capture and/or gamma emission are used in SPECT, and include $^{123}$I and 99mTc.

Where the methods are in vitro, the biological sample can be any sample in which a cell or protein target to be detected may be present, including but not limited to, blood samples (including whole blood, serum, etc.), tissues, whole cells (e.g., intact cells), and tissue or cell extracts. Particularly, detection can be assessed on an extracellular surface of a cell. For example, the tissue sample may be fixed (e.g., by formalin treatment) and may be provided embedded in a support (e.g., in paraffin) or frozen unfixed tissue.

Assays can take a wide variety of forms, such as competition, direct reaction, or sandwich type assays. Examples of assays include Western blots; agglutination tests; enzyme-labeled and mediated immunoassays, such as enzyme-linked immunosorbent assays (ELISAs); biotin/avidin type assays; radioimmunoassays; immunoelectrophoresis; immunoprecipitation, and the like. The reactions generally include detectable labels conjugated to the scaffold. Labels include those that are fluorescent, chemiluminescent, radioactive, enzymatic and/or dye molecules, or other methods for detecting the formation of a complex between an antigen and the scaffold.

The diagnostic imaging assays described herein can be used to determine whether a subject has a disease such as cancer, as well as monitor the progress of treatment in a subject. Thus, the diagnostic assays can inform selection of therapy and treatment regimen by a clinician.

The assay reagents, including the scaffolds and conjugates of the present disclosure, can be provided in kits, with suitable instructions and other necessary reagents, for imaging purposes. The kit can also contain, depending on the particular assay used, suitable labels and other packaged reagents and materials (i.e. wash buffers and the like). Standard immunoassays, such as those described above, can be conducted using these kits.

Where a cytotoxic moiety is more potent when free from the scaffold portion of the conjugates of the present invention, it may be desirable to use a linker group which is cleavable during or upon internalization into a cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No.

4,489,710), by irradiation of a photolabile bond (e.g., U.S. Pat. No. 4,625,014), by hydrolysis of derivatized amino acid side chains (e.g., U.S. Pat. No. 4,638,045), by serum complement-mediated hydrolysis (e.g., U.S. Pat. No. 4,671,958), and acid-catalyzed hydrolysis (e.g., U.S. Pat. No. 4,569,789).

Toxin proteins for use as cytotoxic moieties include ricin, abrin, diphtheria toxin, cholera toxin, gelonin, *Pseudomonas* exotoxin, *Shigella* toxin, pokeweed antiviral protein, and other toxin proteins known in the medicinal biochemistry arts. As these toxin agents may elicit undesirable immune responses in the patient, especially if injected intravascularly, they may be encapsulated in a carrier for coupling to recombinant binding protein scaffolds.

Examples of drugs that may be suitable in the conjugates include, but are not limited to, pyrrolobenzodiazepine (PBD) dimer, tubulin-binders such as, for example, dolastatin 10, monomethyl dolastatin 10, auristain E, monomethyl auristain E (MMAE), auristatin F, monomethyl auristatin F, HTI-286, tubulysin M, maytansinoid AP-3, cryptophycin, Boc-Val-Dil-Dap-OH, tubulysin IM-1, Boc-Val-Dil-Dap-Phe-OMe, tubulysin IM-2, Boc-Nme-Val-Val-Dil-Dap-OH, tubulysin 1M-3, and colchicine DA; DNA-alkylators (duocarmycin analogs) such as, for example, duocarmycin SA, duocarmycin ON, duocarmycin DMG, duocarmycin DMA, duocarmycin MA, duocarmycin TM, duocarmycin MB, duocarmycin GA; tomaymycin DM; SJG-136; illudin S; irofulven; apaziquone; triptolide; staurosporine; camptothecin; methotrexate; and other anti-cancer drugs such as, for example, kinase inhibitors, histone deacetylase (HDAC) inhibitors, proteasome inhibitors, and matrix metalloproteinase (MMP) inhibitors.

It may be desirable to couple more than one therapeutic and/or imaging moiety to a recombinant binding protein scaffold. By forming a fusion protein comprising the scaffolds, several therapeutic strategies may be simultaneously implemented, a scaffold may be made useful as a contrasting agent for several visualization techniques, or a therapeutic scaffold may be labeled for tracking by a visualization technique. In one embodiment, multiple molecules of an imaging or therapeutic moiety are coupled to one scaffold molecule. In another embodiment, more than one type of moiety may be coupled to one scaffold.

Regardless of the particular embodiment, conjugates with more than one moiety may be prepared in a variety of ways. For example, more than one moiety may be coupled directly to a scaffold molecule, or linkers which provide multiple sites for attachment (e.g., dendrimers) can be used. Alternatively, a carrier with the capacity to hold more than one therapeutic or imaging moiety can be used.

A carrier may bear the agents in a variety of ways, including covalent bonding either directly or via a linker group, and non-covalent associations. Suitable covalent-bond carriers include proteins such as albumins (e.g., U.S. Pat. No. 4,507,234), peptides, and polysaccharides such as aminodextran (e.g., U.S. Pat. No. 4,699,784), each of which have multiple sites, for the attachment of moieties. A carrier may also bear an agent by non-covalent associations, such as non-covalent bonding or by encapsulation, such as within a liposome vesicle (e.g., U.S. Pat. Nos. 4,429,008 and 4,873,088). Encapsulation carriers are especially useful for imaging moiety conjugation to recombinant binding protein scaffold moieties. In addition, encapsulation carriers are also useful in therapeutic embodiments, as they can allow the therapeutic compositions to gradually release a therapeutic moiety over time while concentrating it in the vicinity of the tumor cells.

Carriers and linkers specific for radionuclide agents (both for use as cytotoxic moieties or positron-emission imaging moieties) include radiohalogenated small molecules and chelating compounds, such as DOTAP. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis. Such chelation carriers are also useful for magnetic spin contrast ions for use in magnetic resonance imaging tumor visualization methods, and for the chelation of heavy metal ions for use in radiographic visualization methods.

Conjugates are also useful in therapeutic moieties for pharmacokinetic purposes, which may be referred to as a pharmacokinetic moiety. Recombinant binding protein scaffolds have the ability to bind protein targets with high affinity and selectivity. Therapeutic action can thus either be directly carried out by blocking ligand receptor interactions, or by functionalizing the scaffold to have long half-lives and toxic payloads. Recombinant binding protein scaffolds can be fused for example to a small engineered albumin-binding domain (ABD) to increase circulatory half-life, with increased dose to the tumor and reduced kidney uptake; or to a human serum albumin sequence. The scaffolds of the present invention can also be fused to, for example, an Fc sequence, which provides for effector functions, i.e. an effector function moiety, and increased circulatory half-life. The choice of Fc may be based on the desired effector function, e.g. a human Fc sequence including IgGI IgG2a, IgG2b, IgG3, IgG4, IgA, IgM, IgD, IgE, etc. The Fc region optionally provides for dimerization. Alternatively other molecules can be used to increase the serum half-life, including without limitation, polyethylene glycol (PEG), and mimetics thereof.

In the present methods, a recombinant binding protein scaffold may be produced by recombinant methods. The nucleic acid encoding the scaffold can be inserted into a replicable vector for expression. Many such vectors are available. The vector components generally include, but are not limited to, one or more of the following: an origin of replication, one or more marker genes, an enhancer element, a promoter, and a transcription termination sequence. Codon usage may be optimized for the desired host cell.

Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature.

Promoters suitable for use with prokaryotic hosts include the β-lactamase and lactose promoter systems, alkaline phosphatase, a tryptophan (trp) promoter system, and hybrid promoters such as the tac promoter. However, other known bacterial promoters are also suitable. Such nucleotide sequences have been published, thereby enabling a skilled worker operably to ligate them to a DNA coding sequence. Promoters for use in bacterial systems also will contain a Shine-Dalgarno (S.D.) sequence operably linked to the coding sequence.

Promoter sequences are known for eukaryotes. Examples of suitable promoting sequences for use with yeast hosts include the promoters for 3-phosphoglyceratekinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, x-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors used in eukaryotic host cells (yeast, fungi, insect, plant, animal, human, or nucleated cells from other multicellular organisms) may also contain sequences necessary for the termination of transcription and for stabilizing the mRNA. Such sequences are commonly available from the 5' and, occasionally 3', untranslated regions of eukaryotic or viral DNAs or cDNAs.

Construction of suitable vectors containing one or more of the above-listed components employs standard techniques. Isolated plasmids or DNA fragments can be cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. These examples are illustrative rather than limiting.

In addition to prokaryotes, eukaryotic microbes such as filamentous fungi or yeast are suitable expression hosts. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as *K. lactis, K. fragilis*, etc.; *Pichia pastoris; Candida; Neurospora crassa; Schwanniomyces* such as *Schwanniomyces occidentalis*; and filamentous fungi such as *Penicillium, Tolypocladium*, and *Aspergillus* hosts such as *A. nidulan*, and *A. niger*.

Examples of useful mammalian host cell lines are mouse L cells (L-M[TK-], ATCC #CRL-2648), monkey kidney CVT line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MACK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2).

Host cells are transfected with the above-described expression vectors, and cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan. Based on these compositions, disclosed herein are methods of detecting a target in a sample comprising: (a) contacting the target with the recombinant binding protein scaffold comprising a binding domain specific for the target; and (b) detecting binding of the target to the recombinant binding protein scaffold, thereby detecting the target. This method provides a strategy for, inter alia, diagnosing various disease states. The target may comprise a fluid sample, such as biological samples (e.g., cells, blood, tissue).

Also disclosed herein is a polypeptide display library. The polypeptide display library can be used to screen and select molecules with a desired binding affinity to a target ligand.

In some instances, the polypeptide display library is displayed on the surface of a ribosome, bacteriophage (e.g. T4 phage display, T7 phage display, filamentous phage M13), virus, bacteria, yeast, mammalian cell, mRNA, or cDNA. For example, filamentous phage display has been observed to survive extreme selection conditions such as heat (Dudgeon K., et al., 2013) and in vivo selections in live animals (Du B., et al., 2010). For example, the methods herein may include phage display (Ozawa et al., J. Vet. Med. Sci. 67(12):1237-41, 2005), yeast display (Boder et al., Nat. Biotech. 15:553-57, 1997), ribosome display (Hanes et al., PNAS 94:4937-42, 1997; Lipovsek et al., J. Imm. Methods, 290:51-67, 2004), bacterial display (Francisco et al., PNAS 90:10444-48, 1993; Georgiou et al., Nat. Biotech. 15:29-34, 1997), mRNA display (Roberts et al., PNAS 94:12297-302, 1997; Keefe et al., Nature 410:715-18, 2001), and protein scaffold libraries (Hosse et al., Protein Science 15:14-27, 2006).

The polypeptide library may include a population of proteins containing mutations introduced by random mutagenesis and/or rational design mutagenesis. The present disclosure provides methods for obtaining a recombinant protein scaffold that binds to a desired target comprising (a) contacting a target ligand with the polypeptide display library under conditions that allow a scaffold:target ligand complex to form, and (b) obtaining from the complex, the scaffold that binds the target ligand. Affinity characteristics to a target ligand may be used to select one or more recombinant binding protein scaffolds produced after step (b). Further library randomizations of the product of step (b) may provide addition affinity maturation of the scaffold.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. Efforts have been made to ensure accuracy with respect to numbers (e.g., amounts, temperatures, etc.); however, some errors and deviations should be accounted for. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1: Pilot $^{Tm}$CSP Phage Display Library Construction

Figure 12:
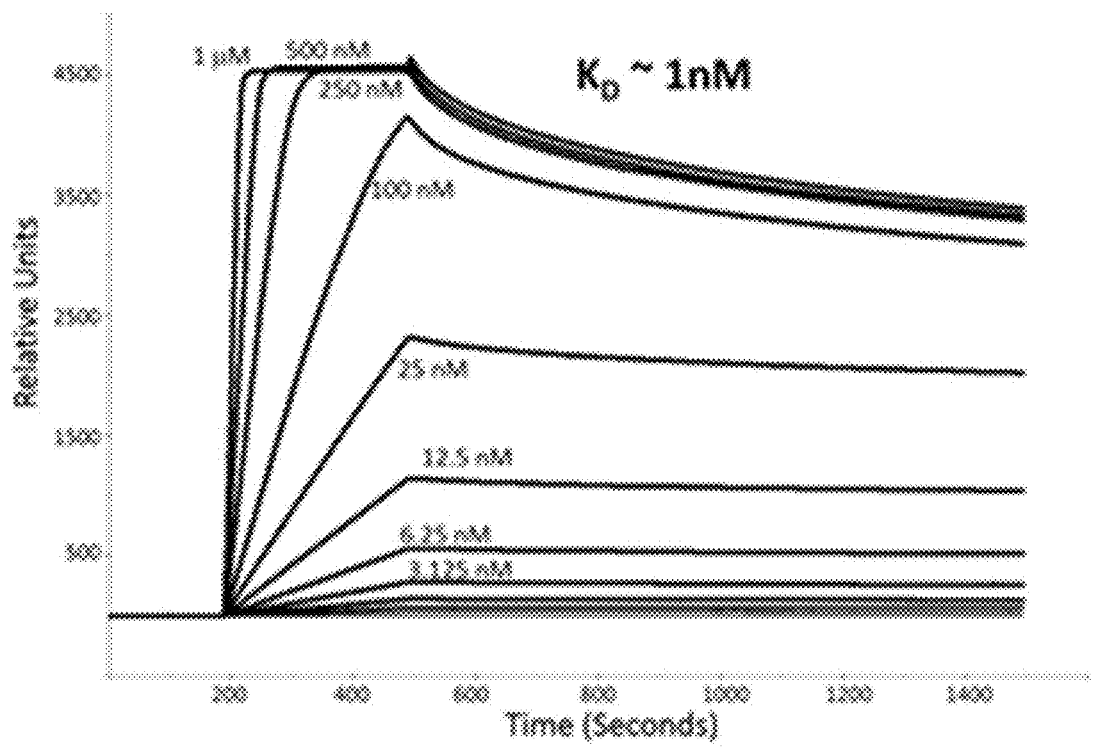
FIG. 12 depicts a plot showing binding curves obtained using a Biacore 3000 and Biaevaluation software.
Figure 13:
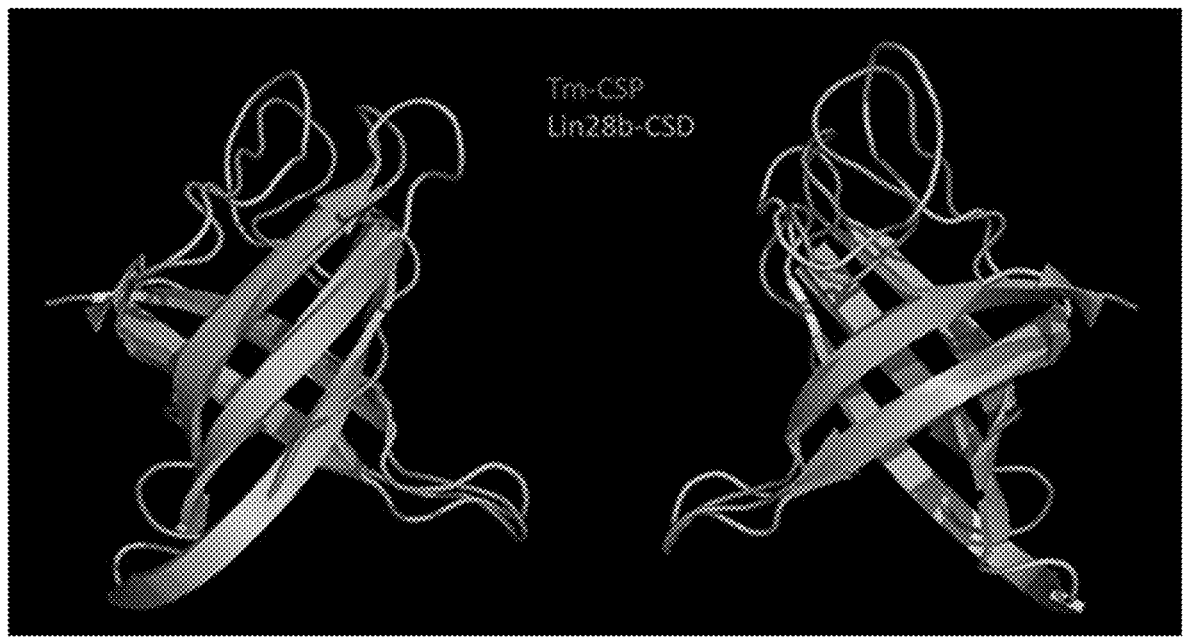
FIG. 13 depicts a $^{Tm}$CSP protein backbone aligned with the cold-shock domain (CSD) of the human Lin28b protein. RMSD for this alignment is 1.94.

Cold-Shock Protein Synthesis and Isolation. The Cold-Shock Protein derived from an extremophilic bacterium *Thermotoga maritima* ($^{Tm}$CSP) is chosen as the basis for the protein scaffold library. $^{Tm}$CSP is synthesized using solid phase protein synthesis ("SPPS") and the resulting crude product is purified by reverse phase high performance liquid chromatography ("RP-HPLC"). The resulting purified protein independently folds into a functional structure capable of binding its natural target (polyT-ssDNA) with a KD of ~1 nM (FIG. 12). The solution NMR structure of $^{Tm}$CSP is available (PDB ID: 1G6P) which enabled the identification of surface exposed amino acid side chains for the design and engineering of combinatorial display libraries.

Figure 7:
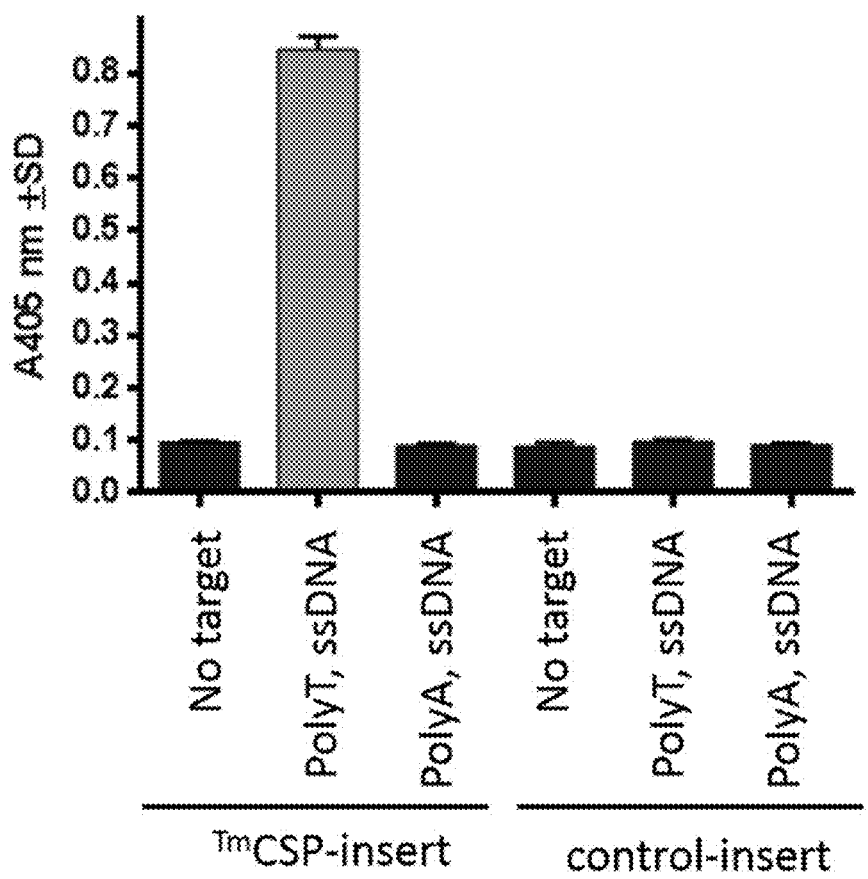
FIG. 7 depicts ELISA confirmation of functional wild-type $^{Tm}$CSP expressed on the surface of T7 phage through specific binding to immobilized polyT-ssDNA detected with anti-T7 tail fiber antibody.

Cold-Shock Protein functional display on T7 phage. $^{Tm}$CSP has many natural characteristics, with benefits over antibodies, which drove selection of this scaffold for the design of engineered binding proteins (Table 1). Since expression of a functional protein fused with a phage coat protein is required to enable phage display screening, functional expression of $^{Tm}$CSP on the surface capsid protein of T7 phage using the T7 Select-10 vector (Novagen) was first confirmed, expressing an average of ten copies of $^{Tm}$CSP per phage particle. A double stranded DNA insert encoding $^{Tm}$CSP was synthesized and ligated into the T7 genome to create an in-frame capsid fusion. The resulting $^{Tm}$CSP-phage specifically bound polyT-ssDNA ensuring functional display on the surface and suggesting amenability of this scaffold to combinatorial screening using T7 phage. FIG. 4 shows ELISA data confirming the expression of ssDNA binding phage (CSP WT). Control phage and phage displaying $^{Tm}$CSP Y14A, F16A, F26A, H28Q containing four mutations of the DNA binding site result in no or diminished ss-polyT DNA binding. FIG. 7 shows a similar assay, wherein $^{Tm}$CSP displayed on phage specifically bound polyT ssDNA and not polyA ssDNA.

Figure 14:
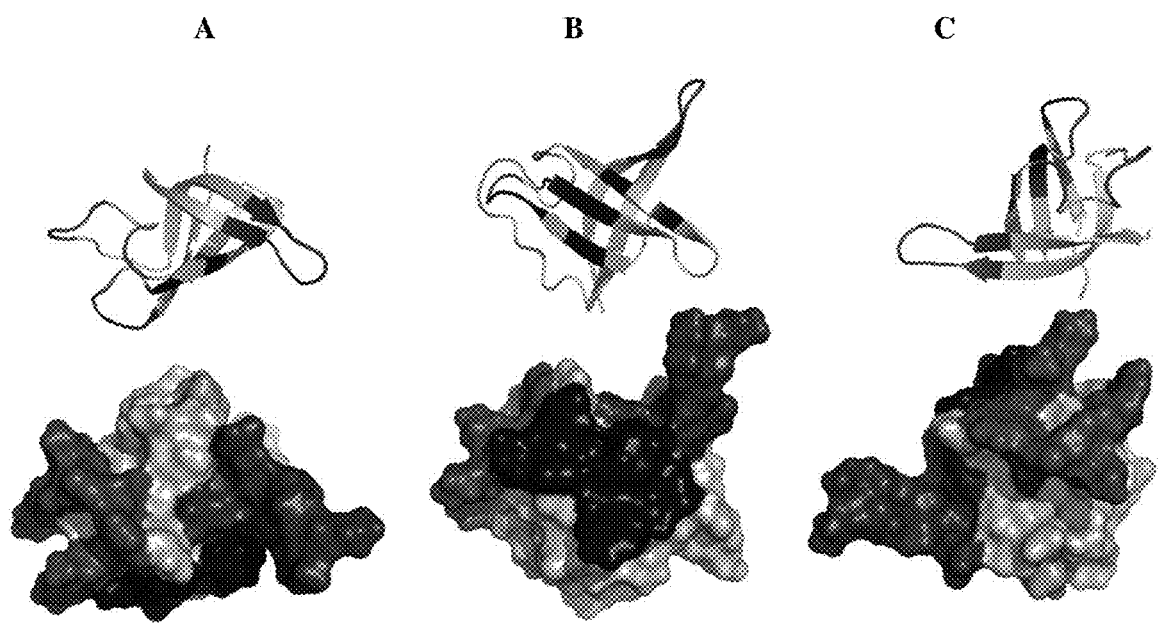
FIG. 14A-C depicts three (A-C) different views of $^{Tm}$CSP, including a cartoon showing secondary structure and a surface map, showing the locations of amino acids to be randomized in for libraries $^{Tm}$CSP-L, $^{Tm}$CSP-F and $^{Tm}$CSP-K. N- and C-terminal amino acids are also shown. The sequence pictured is SEQ ID NO: 1.

Pilot Cold-Shock Protein targeted randomized phage display library construction. Three regions were identified, each made up of 8 surface exposed amino acid sidechains, with which to create phage display libraries. The first region for randomization contains residues located in the loop between β-sheets 1 and 2 as well as the loop between β-sheets 3 and 4. This region contains loops without helical or β-sheets secondary structure, held in place by the stable interactions of the 5 β-sheet core structure, reminiscent of complementarity determining regions of antibodies. Amino acids 10-12, 29, 30 and 35-37 are randomized to create phage display library $^{Tm}$CSP-L (FIG. 14). The second region for randomization is made up of surface exposed amino acids on the face of antiparallel β-sheets 1-3 for which amino acids 6,7,9,14-16, 24 and 26 is randomized to create phage display library $^{Tm}$CSP-F (FIG. 14). The third region for randomization is made up of a β-turn and part of antiparallel β-sheets 4 and 5, which extends out of the core structure like a key for which amino acids 51-58 are randomized to create phage display library $^{Tm}$CSP-K (FIG. 14). The three regions chosen for randomization purposefully do not include the N- or C terminal residues which enables the use of purification tags (His6), detection tags (HA or FLAG), a cysteine residue for site specific labelling or dimerization, or proteolytic degradation sequence fusion proteins. Randomization of amino acid residues implicated in thermal stability are avoided or limited in each library design (80-82).

Figure 15:
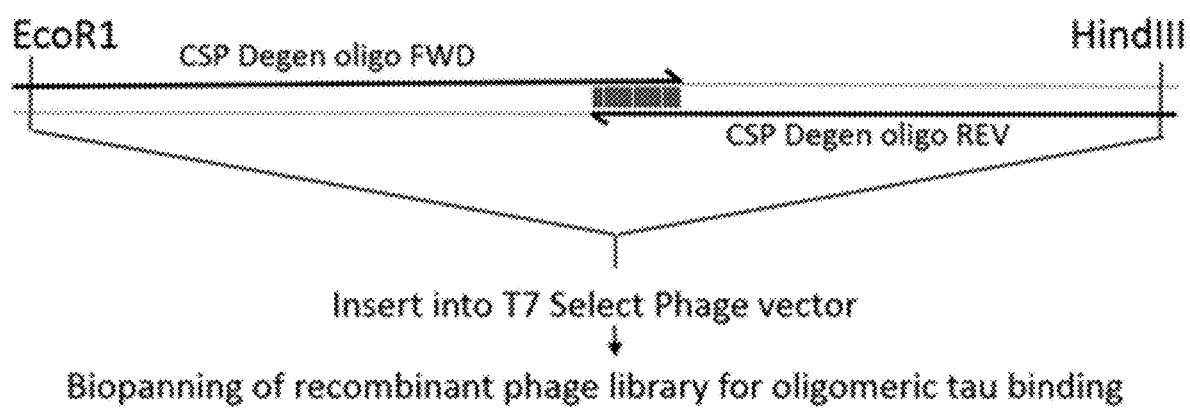
FIG. 15 depicts $^{Tm}$CSP phage display library strategy depicting the annealing and polymerization of two long oligonucleotides with overlapping complementarity that together encode the entire $^{Tm}$CSP cDNA containing selected degenerate codons.

A pilot $^{Tm}$CSP-L library using the T7 Select phage display system was constructed in Example 1, which was randomized at 8 amino acid positions using the method described in FIG. 1. The actual library diversity was calculated at $6.7 \times 10^7$ and the theoretical protein diversity for the VNK codon (which encodes only 16 amino acids and no stop codons) used to randomize 8 amino acid positions is $4 \times 10^9$. By scaling up (12x) the $^{Tm}$CSP-L VNK library using two T7 Select phage display kits, the final naïve $^{Tm}$CSP-L library has a diversity of $>3 \times 10^8$. With the completion of three libraries ($^{Tm}$CSP-L, $^{Tm}$CSP-F and $^{Tm}$CSP-K), one tripartite library with a diversity of $~1 \times 10^9$ unique clones is created utilizing three very different structural architectures on the same scaffold. A double stranded DNA insert library encoding $^{Tm}$CSP with targeted randomized codons was synthesized and ligated into the T7 genome to create an in-frame capsid fusion. The resulting ligated T7 genes were packaged into active phage using commercial T7 packaging extracts. FIGS. 1 and 15 represent overviews of two molecular strategies used to create pilot libraries. The raw diversity of the pilot library was $6.7\times10^7$ unique clones. 21 random clones were then isolated and the CSP insertion region was sequenced for each. The translation products are shown in FIG. 3. 18 of 21 clones demonstrated intact full-length clones with degeneracies only in the desired codons. 3 of 21 clones demonstrated either frameshift mutations of deletions. This suggests ~86% of unique clones are desirable full-length CSP variants. These demonstrated marked improvements upon optimization of this strategy where the raw diversity was increased from $1.8\times10^6$ to $6.7\times10^7$ and the percent of correct clones increased from 75% to 86%. This pilot library is an example of a library with 8 surface exposed amino acids randomized as shown in FIGS. 8A and 8D and in FIG. 14A. This pilot library strategy can be scaled up for larger libraries or translated to other surface display systems such as M13 phage display.

Example 2: Panning of Pilot $^{Tm}$CSP Phage Display Library for Tau Binders

Panning of the pilot $^{Tm}$CSP Phage Display Library Against Tau Protein.

Recombinant tau protein was immobilized to wells of a 96 well ELISA plate. Wells were incubates in a 5% milk or Bovine serum albumin solution to block non-specific binding sites. Tau containing wells and control wells were incubated with high titers of amplified pilot library before undergoing between 3 and 10 washes in buffer. Bound phage were collected by elution in a 10% SDS elution buffer. Eluates were diluted and used to titer the amount of panned phage and to inoculate liquid cultures of T7 phage competent bacteria for amplification of the panned phage. Amplified panned phage were then used for another round of panning against tau protein. Three rounds of panning were completed and 20 random clones from the final panning were amplified for ELISA analysis.

Anti-tau phage ELISA of panned clones: Wells are coated with recombinant tau protein and incubated with T7 phage derived from a single plaque/clone. Binding of phage to tau is detected using a monoclonal T7 tail fiber antibody and alkaline phosphatase conjugated secondary antibody (as shown in FIG. 9). Some clones from the panned library showed binding of tau relative to the control CSP-WT phage suggesting that panning from these libraries will allow identification of tau binding constructs. Panning from a library with larger diversity will increase the likelihood of developing high affinity binders using this strategy.

TABLE 1

| Attribute of ™ CSP | Benefit over antibodies |
|---|---|
| Extremely Stable, 87° C. melting temp | Stable scaffold to support surface amino acid changes or other engineering. |
| Single chain construct, monomeric | No multimeric assembly, ease of protein folding for synthesis and expression. |
| Cysteineless, Disulfide-free | Functional stability in the reducing cytoplasmic environment. |
| Independently folded | No chaperones required, enables synthetic production or functional expression. |
| Reversible denaturation | Likelihood of correct folding with protein transduction domain delivery. |
| Small Size, ~7.5 kDa | Better tissue extravasation renal clearance, simpler folding. |

Example 3: Development of PHF6 Sequence-Containing $^{Tm}$CSP-Derived Proteins Through Rational Design Design of PHF6-containing $^{Tm}$CSP variants. Tau aggregates in the form of paired helical filaments (PHF) are a hallmark of certain neurodegenerative diseases. The core of these PHF fibrils are composed of an orderly stacking of a region in the repeat domain of tau. Part of this region includes the PHF6 sequence SEQ ID NOS: 31 (VQIVYK) and PHF6* sequence SEQ ID NO: 32 (VQIINK). Peptides, cyclic peptides and peptidomimetics of these sequences have been used to bind to and/or inhibit elongation of the tau PHF. Here, rationally designed PHF6 and PHF6* sequences were introduced into the $^{Tm}$CSP scaffold in order to create a stabilized form of PHF6. These sequences were rationally designed into an extension antiparallel beta sheets 4 and 5, which includes a beta turn. Pictorial representations of the rationally designed constructs are shown in FIGS. 10 and 16. FIG. 11 demonstrates combinations of rationally designed constructs using PHF6 or PHF6* sequences as well as different linkers and beta turn amino acids.

Evaluation of recombinant PHF6-containing $^{Tm}$CSP variants on in vitro tau aggregation. Recombinant $^{Tm}$CSP proteins with engineered PHF regions designed to interact with tau fibrils are made in *E. coli* and purified. Recombinant $^{Tm}$CSP proteins are added to in vitro tau aggregation assays to determine whether there is a direct influence on tau aggregation. Certain natural chaperone proteins molecular chaperones have been shown to modulate tau aggregation in vitro, and a similar assays is used to evaluate anti-tau $^{Tm}$CSP constructs. A small number of rationally designed $^{Tm}$CSP constructs are developed with an engineered domain designed to mimic the PHF6 region of tau that makes up part of the core of fibrillar aggregates. These constructs were produced recombinantly in *E. coli* and purified, then tested with an in vitro heparin-induced aggregation assay of tau P301L (FIG. 5). $^{Tm}$CSP-PHF6 did reduce the total intensity of thioflavin T signal relative to T-CSP-WT, suggesting an overall reduction in tau aggregation. This data supports modulation of tau aggregation by tau targeted $^{Tm}$CSP variants. Controls in the absence of Tau P301L demonstrated no aggregation.

Evaluation of PHF6-containing $^{Tm}$CSP variant constructs by transient transfection of expression plasmids in a cell model of tau aggregation. For evaluation of effects of $^{Tm}$CSP variants on tau in cells, the metric is based on cotransfections of tau (WT or an aggregation prone mutant P301L/S320F) and anti-tau $^{Tm}$CSP plasmids (or anti-tau $^{Tm}$CSP fusion protein) in HEK293T cells. $^{Tm}$CSP variants were subcloned into pCMV6 mammalian expression vectors. HEK293T cells co-transfected with plasmids encoding either tau WT or tau P301L/S320F and a control or antitau $^{Tm}$CSP protein are lysed two days post-transfection in lysis buffer containing 1% Triton X-100, protease inhibitors, and phosphatase inhibitors. Cells are incubated for 20 minutes at 4° C. and cleared by centrifugation at 10,000×g. Cleared lysates are ultracentrifuged at 100,000×g to pellet the Triton Insoluble fraction. The Triton-insoluble pellet is washed and solubilized in an 8M Urea buffer and samples are evaluated by SDS-PAGE and Western blot with anti-tau as shown in FIG. 6. The evaluation consists of total tau protein levels (as an indicator of clearance), and tau levels in a Triton-insoluble fractions (as an indicator of aggregation). FIG. 6 demonstrates that the construct FLAG-CSP-PHF6-1 co-expression in this cell model results in decreased expression of tau WT and tau P301L/S320F. A corresponding reduction in tau in the Triton insoluble fraction is also observed, suggesting a reduction in the accumulation of aggregated tau.

While direct binding of the small $^{Tm}$CSP scaffold to tau may induce effects on cellular tau in some cases, fusion proteins can be developed that tether the tau binding affinity of $^{Tm}$CSP variants to another domain to facilitate modulation of tau. First, an anti-tau $^{Tm}$CSP-GFP adds steric bulk to the $^{Tm}$CSP, which may facilitate an inhibition of tau aggregation. Second, anti-tau $^{Tm}$CSP proteins fused with proteolytic degradation signals such as ubiquitin, ubiquitin K48R, ubiquitin K63R, CMA-(MARVKKDQAEPLHRKFERQPPG, SEQ ID NO: 35) or a PEST degron-(SHGFPPEVEEQDDGTLPMSCAQESGMDRHPAACASARINV, SEQ ID NO: 36), may facilitate enhanced clearance of the engineered protein and may also enhance clearance of the targeted tau protein (59, 62, 63). Third, anti-tau $^{Tm}$CSP proteins can be fused to molecular chaperones (or domains of molecular chaperones) to create a bifunctional fusion protein. For example, Cyp40 has been shown not only to prevent tau aggregation, but to unravel preformed aggregates (45). An anti-tau $^{Tm}$CSP-Cyp40 fusion protein may enhance the effect of Cyp40 by providing specificity of binding to epitopes of tau. FIG. 6 demonstrates an analysis of FLAG-CMA-CSP-PHF6, which appears to reduce the accumulation of tau WT, but not tau P301L/S320F.

REFERENCES

1. Roberson, E. D., Scearce-Levie, K., Palop, J. J., Yan, F., Cheng, I. H., Wu, T., Gerstein, H., Yu, G.-Q., and Mucke, L. (2007) Reducing endogenous tau ameliorates amyloid beta-induced deficits in an Alzheimer's disease mouse model. *Science.* 316, 750-754
2. Leroy, K., Ando, K., Laporte, V., Dedecker, R., Suain, V., Authelet, M., Heraud, C., Pierrot, N., Yilmaz, Z., Octave, J.-N., and Brion, J.-P. (2012) Lack of tau proteins rescues neuronal cell death and decreases amyloidogenic processing of APP in APP/PS1 mice. *Am. J. Pathol.* 181, 1928-1940
3. Hurtado, D. E., Molina-Porcel, L., Iba, M., Aboagye, A. K., Paul, S. M., Trojanowski, J. Q., and Lee, V. M.-Y. (2010) A{beta} accelerates the spatiotemporal progression of tau pathology and augments tau amyloidosis in an Alzheimer mouse model. *Am. J Pathol.* 177, 1977-1988
4. Rapoport, M., Dawson, H. N., Binder, L. I., Vitek, M. P., and Ferreira, A. (2002) Tau is essential to beta-amyloid-induced neurotoxicity. *Proc. Natl. Acad. Sci. U.S.A.* 99, 6364-6369
5. Nussbaum, J. M., Schilling, S., Cynis, H., Silva, A., Swanson, E., Wangsanut, T., Tayler, K., Wiltgen, B., Hatami, A., Ronicke, R., Reymann, K., Hutter-Paier, B., Alexandru, A., Jagla, W., Graubner, S., Glabe, C. G., Demuth, H.-U., and Bloom, G. S. (2012) Prion-like behaviour and tau-dependent cytotoxicity of pyroglutamylated amyloid-β. *Nature.* 485, 651-655
6. Shipton, O. A., Leitz, J. R., Dworzak, J., Acton, C. E. J., Tunbridge, E. M., Denk, F., Dawson, H. N., Vitek, M. P., Wade-Martins, R., Paulsen, O., and Vargas-Caballero, M. (2011) Tau protein is required for amyloid {beta}-induced impairment of hippocampal long-term potentiation. *J. Neurosci.* 31, 1688-1692
7. Bloom, G. S. (2014) Amyloid-O and tau: the trigger and bullet in Alzheimer disease pathogenesis. *JAMA Neurol.* 71, 505-508
8. Binder, L. I., Frankfurter, A., and Rebhun, L. I. (1985) The distribution of tau in the mammalian central nervous system. *J Cell Biol.* 101, 1371-1378
9. Kowall, N. W., and Kosik, K. S. (1987) Axonal disruption and aberrant localization of tau protein characterize the neuropil pathology of Alzheimer's disease. *Ann. Neurol.* 22, 639-643
10. Lippens, G., Sillen, A., Landrieu, I., Amniai, L., Sibille, N., Barbier, P., Leroy, A., Hanoulle, X., and Wieruszeski, J.-M. (2007) Tau Aggregation in Alzheimer's Disease. *Prion.* 1, 21-25
11. Cohen, T. J., Guo, J. L., Hurtado, D. E., Kwong, L. K., Mills, I. P., Trojanowski, J. Q., and Lee, V. M. Y. (2011) The acetylation of tau inhibits its function and promotes pathological tau aggregation. *Nat Commun.* 2, 252
12. Lee, S., and Shea, T. B. (2012) Caspase-Mediated Truncation of Tau Potentiates Aggregation. *International Journal of Alzheimer's Disease.* 2012, e731063
13. Meraz-Rios, M. A., Lira-De Leon, K. I., Campos-Pena, V., De Anda-Hernandez, M. A., and Mena-Lopez, R. (2010) Tau oligomers and aggregation in Alzheimer's disease. *Journal of Neurochemistry.* 112, 1353-1367
14. Peeraer, E., Bottelbergs, A., Van Kolen, K., Stancu, I.-C., Vasconcelos, B., Mahieu, M., Duytschaever, H., Ver Donck, L., Torremans, A., Sluydts, E., Van Acker, N., Kemp, J. A., Mercken, M., Brunden, K. R., Trojanowski, J. Q., Dewachter, I., Lee, V. M. Y., and Moechars, D. (2015) Intracerebral injection of preformed synthetic tau fibrils initiates widespread tauopathy and neuronal loss in the brains of tau transgenic mice. *Neurobiol. Dis.* 73, 83-95
15. Clavaguera, F., Bolmont, T., Crowther, R. A., Abramowski, D., Frank, S., Probst, A., Fraser, G., Stalder, A. K., Beibel, M., Staufenbiel, M., Jucker, M., Goedert, M., and Tolnay, M. (2009) Transmission and spreading of tauopathy in transgenic mouse brain. *Nat. Cell Biol.* 11, 909-913
16. Santacruz, K., Lewis, J., Spires, T., Paulson, J., Kotilinek, L., Ingelsson, M., Guimaraes, A., DeTure, M., Ramsden, M., McGowan, E., Forster, C., Yue, M., Ome, J., Janus, C., Mariash, A., Kuskowski, M., Hyman, B., Hutton, M., and Ashe, K. H. (2005) Tau suppression in a neurodegenerative mouse model improves memory function. *Science.* 309, 476-481
17. Cardenas-Aguayo, M. del C., Gomez-Virgilio, L., DeRosa, S., and Meraz-Rios, M. A. (2014) The Role of Tau Oligomers in the Onset of Alzheimer's Disease Neuropathology. *ACS Chem. Neurosci.* 5, 1178-1191
18. Castillo-Carranza, D. L., Gerson, J. E., Sengupta, U., Guerrero-Munoz, M. J., Lasagna-Reeves, C. A., and Kayed, R. (2014) Specific Targeting of Tau Oligomers in Htau Mice Prevents Cognitive Impairment and Tau Toxicity Following Injection with Brain-Derived Tau Oligomeric Seeds. *Journal of Alzheimer's Disease.* 40, S97-S111
19. Cleary, J. P., Walsh, D. M., Hofmeister, J. J., Shankar, G. M., Kuskowski, M. A., Selkoe, D. J., and Ashe, K. H. (2005) Natural oligomers of the amyloid-beta protein specifically disrupt cognitive function. *Nat. Neurosci.* 8, 79-84
20. Patterson, K. R., Remmers, C., Fu, Y., Brooker, S., Kanaan, N. M., Vana, L., Ward, S., Reyes, J. F., Philibert, K., Glucksman, M. J., and Binder, L. I. (2011) Characterization of prefibrillar Tau oligomers in vitro and in Alzheimer disease. *J. Biol. Chem.* 286, 23063-23076
21. Walsh, D. M., Klyubin, I., Fadeeva, J. V., Cullen, W. K., Anwyl, R., Wolfe, M. S., Rowan, M. J., and Selkoe, D. J.

21. (2002) Naturally secreted oligomers of amyloid beta protein potently inhibit hippocampal long-term potentiation in vivo. *Nature.* 416, 535-539
22. Sigurdsson, E. M. (2016) Tau Immunotherapy. *NDD.* 16, 34-38
23. Pedersen, J. T., and Sigurdsson, E. M. (2015) Tau immunotherapy for Alzheimer's disease. *Trends Mol Med.* 21, 394-402
24. Boutajangout, A., Quartermain, D., and Sigurdsson, E. M. (2010) Immunotherapy targeting pathological tau prevents cognitive decline in a new tangle mouse model. *J Neurosci.* 30, 16559-16566
25. Chai, X., Wu, S., Murray, T. K., Kinley, R., Cella, C. V., Sims, H., Buckner, N., Hanmer, J., Davies, P., O'Neill, M. J., Hutton, M. L., and Citron, M. (2011) Passive Immunization with Anti-Tau Antibodies in Two Transgenic Models REDUCTION OF TAU PATHOLOGY AND DELAY OF DISEASE PROGRESSION. *J. Biol. Chem.* 286, 34457-34467
26. Sankaranarayanan, S., Barten, D. M., Vana, L., Devidze, N., Yang, L., Cadelina, G., Hoque, N., DeCarr, L., Keenan, S., Lin, A., Cao, Y., Snyder, B., Zhang, B., Nitla, M., Hirschfeld, G., Barrezueta, N., Polson, C., Wes, P., Rangan, V. S., Cacace, A., Albright, C. F., Meredith, J., Trojanowski, J. Q., Lee, V. M.-Y., Brunden, K. R., and Ahlijanian, M. (2015) Passive immunization with phospho-tau antibodies reduces tau pathology and functional deficits in two distinct mouse tauopathy models. *PLoS ONE.* 10, e0125614
27. Ising, C., Gallardo, G., Leyns, C. E. G., Wong, C. H., Stewart, F., Koscal, L. J., Roh, J., Robinson, G. O., Serrano, J. R., and Holtzman, D. M. (2017) AAV-mediated expression of anti-tau scFvs decreases tau accumulation in a mouse model of tauopathy. *Journal of Experimental Medicine.* 10.1084/jem.20162125
28. Gu, J., Congdon, E. E., and Sigurdsson, E. M. (2013) Two Novel Tau Antibodies Targeting the 396/404 Region Are Primarily Taken Up by Neurons and Reduce Tau Protein Pathology. *J Biol. Chem.* 288, 33081-33095
29. Collin, L., Bohrmann, B., Gopfert, U., Oroszlan-Szovik, K., Ozmen, L., and Gruninger, F. (2014) Neuronal uptake of tau/pS422 antibody and reduced progression of tau pathology in a mouse model of Alzheimer's disease. *Brain.* 137, 2834-2846
30. Colby, D. W., Garg, P., Holden, T., Chao, G., Webster, J. M., Messer, A., Ingram, V. M., and Wittrup, K. D. (2004) Development of a human light chain variable domain (V(L)) intracellular antibody specific for the amino terminus of huntingtin via yeast surface display. *J. Mol. Biol.* 342, 901-912
31. Colby, D. W., Chu, Y., Cassady, J. P., Duennwald, M., Zazulak, H., Webster, J. M., Messer, A., Lindquist, S., Ingram, V. M., and Wittrup, K. D. (2004) Potent inhibition of huntingtin aggregation and cytotoxicity by a disulfide bond-free single-domain intracellular antibody. *Proc. Natl. Acad. Sci. U.S.A.* 101, 17616-17621
32. Visintin, M., Settanni, G., Maritan, A., Graziosi, S., Marks, J. D., and Cattaneo, A. (2002) The intracellular antibody capture technology (IACT): towards a consensus sequence for intracellular antibodies11 Edited by J. Kam. *Journal of Molecular Biology.* 317, 73-83
33. Levites, Y., Golde, T., Cruz, P. E., Rosario, A. M., and Sinyavskiy, G. D. (2015) Functionalized intrabodies as potential tau targeting therapy. *Alzheimer's & Dementia: The Journal of the Alzheimer's Association.* 11, P227
34. Fiedler, M., and Skerra, A. (2014) Non-Antibody Scaffolds as Alternative Therapeutic Agents. In *Handbook of Therapeutic Antibodies* (Dubel, S., and Reichert, J. M. eds), pp. 435-474, Wiley-VCH Verlag GmbH & Co. KGaA, 10.1002/9783527682423.ch17
35. Owens, B. (2017) Faster, deeper, smaller—the rise of antibody-like scaffolds. *Nature Biotechnology.* 35, nbt0717-602-602
36. Lofblom, J., Feldwisch, J., Tolmachev, V., Carlsson, J., Stahl, S., and Frejd, F. Y. (2010) Affibody molecules: Engineered proteins for therapeutic, diagnostic and biotechnological applications. *FEBS Letters.* 584, 2670-2680
37. Miersch, S., and Sidhu, S. S. (2016) Intracellular targeting with engineered proteins. *F1000Res.* 10.12688/f1000research.8915.1
38. Cherf, G. M., and Cochran, J. R. (2015) Applications of yeast surface display for protein engineering. *Methods Mol Biol.* 1319, 155-175
39. Karatan, E., Han, Z., and Kay, B. (2006) Molecular Display Technologies. in *Reviews in Cell Biology and Molecular Medicine*, Wiley-VCH Verlag GmbH & Co. KGaA, 10.1002/3527600906.mcb.200400086
40. Koga, H., Martinez-Vicente, M., Macian, F., Verkhusha, V. V., and Cuervo, A. M. (2011) A photoconvertible fluorescent reporter to track chaperone-mediated autophagy. *Nat Commun.* 2, 386
41. Kaushik, S., and Cuervo, A. M. (2012) Chaperone-mediated autophagy: a unique way to enter the lysosome world. *Trends Cell Biol.* 22, 407-417
42. Bauer, P. O., Goswami, A., Wong, H. K., Okuno, M., Kurosawa, M., Yamada, M., Miyazaki, H., Matsumoto, G., Kino, Y., Nagai, Y., and Nukina, N. (2010) Harnessing chaperone-mediated autophagy for the selective degradation of mutant huntingtin protein. *Nat Biotech.* 28, 256-263
43. Baker, J. D., Shelton, L. B., Zheng, D., Favretto, F., Nordhues, B. A., Darling, A., Sullivan, L. E., Sun, Z., Solanki, P. K., Martin, M. D., Suntharalingam, A., Sabbagh, J. J., Becker, S., Mandelkow, E., Uversky, V. N., Zweckstetter, M., Dickey, C. A., Koren, J., and Blair, L. J. (2017) Human cyclophilin 40 unravels neurotoxic amyloids. *PLoS Biol.* 15, e2001336
44. Blair, L. J., Nordhues, B. A., Hill, S. E., Scaglione, K. M., O'Leary, J. C., Fontaine, S. N., Breydo, L., Zhang, B., Li, P., Wang, L., Cotman, C., Paulson, H. L., Muschol, M., Uversky, V. N., Klengel, T., Binder, E. B., Kayed, R., Golde, T. E., Berchtold, N., and Dickey, C. A. (2013) Accelerated neurodegeneration through chaperone-mediated oligomerization of tau. *J Clin Invest.* 123, 4158-4169
45. Guidotti, G., Brambilla, L., and Rossi, D. (2017) Cell-Penetrating Peptides: From Basic Research to Clinics. *Trends in Pharmacological Sciences.* 38, 406-424
46. Simonato, M., Bennett, J., Boulis, N. M., Castro, M. G., Fink, D. J., Goins, W. F., Gray, S. J., Lowenstein, P. R., Vandenberghe, L. H., Wilson, T. J., Wolfe, J. H., and Glorioso, J. C. (2013) Progress in gene therapy for neurological disorders. *Nat Rev Neurol.* 9, 277-291
47. Naldini, L. (2015) Gene therapy returns to centre stage. *Nature.* 526, 351-360
48. Saint-Aubert, L., Lemoine, L., Chiotis, K., Leuzy, A., Rodriguez-Vieitez, E., and Nordberg, A. (2017) Tau PET imaging: present and future directions. *Molecular Neurodegeneration.* 12, 19
49. Ng, K. P., Pascoal, T. A., Mathotaarachchi, S., Therriault, J., Kang, M. S., Shin, M., Guiot, M.-C., Guo, Q., Harada, R., Comley, R. A., Massarweh, G., Soucy, J.-P., Okamura, N., Gauthier, S., and Rosa-Neto, P. (2017) Monoamine oxidase B inhibitor, selegiline, reduces 18F-THK5351 uptake in the human brain. *Alzheimer's Research & Therapy.* 9, 25
50. Krishnaswamy, S., Lin, Y., Rajamohamedsait, W. J., Rajamohamedsait, H. B., Krishnamurthy, P., and Sigurdsson, E. M. (2014) Antibody-derived in vivo imaging of tau pathology. *J. Neurosci.* 34, 16835-16850
51. Peretti, D., Bastide, A., Radford, H., Verity, N., Molloy, C., Martin, M. G., Moreno, J. A., Steinert, J. R., Smith, T., Dinsdale, D., Willis, A. E., and Mallucci, G. R. (2015) RBM3 mediates structural plasticity and protective effects of cooling in neurodegeneration. *Nature.* 518, 236-239
52. Webster, J. M., Zhang, R., Gambhir, S. S., Cheng, Z., and Syud, F. A. (2009) Engineered two-helix small proteins for molecular recognition. *Chembiochem.* 10, 1293-1296
53. Miao, Z., Ren, G., Jiang, L., Liu, H., Webster, J. M., Zhang, R., Namavari, M., Gambhir, S. S., Syud, F., and Cheng, Z. (2011) A novel 18F-labeled two-helix scaffold protein for PET imaging of HER2-positive tumor. *Eur. J. Nucl. Med. Mol. Imaging.* 38, 1977-1984
54. Ren, G., Zhang, R., Liu, Z., Webster, J. M., Miao, Z., Gambhir, S. S., Syud, F. A., and Cheng, Z. (2009) A 2-helix small protein labeled with 68Ga for PET imaging of HER2 expression. *J. Nucl. Med.* 50, 1492-1499
55. Ren, G., Webster, J. M., Liu, Z., Zhang, R., Miao, Z., Liu, H., Gambhir, S. S., Syud, F. A., and Cheng, Z. (2012) In vivo targeting of HER2-positive tumor using 2-helix affibody molecules. *Amino Acids.* 43, 405-413
56. Cheng, Z., De Jesus, O. P., Namavari, M., De, A., Levi, J., Webster, J. M., Zhang, R., Lee, B., Syud, F. A., and Gambhir, S. S. (2008) Small-animal PET imaging of human epidermal growth factor receptor type 2 expression with site-specific 18F-labeled protein scaffold molecules. *J Nucl. Med.* 49, 804-813
57. Cheng, Z., De Jesus, O. P., Kramer, D. J., De, A., Webster, J. M., Gheysens, O., Levi, J., Namavari, M., Wang, S., Park, J. M., Zhang, R., Liu, H., Lee, B., Syud, F. A., and Gambhir, S. S. (2010) 64Cu-labeled affibody molecules for imaging of HER2 expressing tumors. *Mol Imaging Biol.* 12, 316-324
58. Huber, R., Langworthy, T. A., Konig, H., Thomm, M., Woese, C. R., Sleytr, U. B., and Stetter, K. O. (1986) *Thermotoga maritima* sp. nov. represents a new genus of unique extremely thermophilic eubacteria growing up to 90° C. *Arch. Microbiol.* 144, 324-333
59. Seidler, P., Boyer, D., Rodriguez, J., Sawaya, M., Cascio, D., Murray, K., Gonen, T., and Eisenberg, D. (2018) Structure-based inhibitors of tau aggregation. *Nat Chem.* 10, 170-176
60. Tych, K. M., Batchelor, M., Hoffmann, T., Wilson, M. C., Hughes, M. L., Paci, E., Brockwell, D. J., and Dougan, L. (2016) Differential Effects of Hydrophobic Core Packing Residues for Thermodynamic and Mechanical Stability of a Hyperthermophilic Protein. *Langmuir.* 32, 7392-7402
61. Motono, C., Gromiha, M. M., and Kumar, S. (2008) Thermodynamic and kinetic determinants of *Thermotoga maritima* cold shock protein stability: A structural and dynamic analysis. *Proteins.* 71, 655-669
62. Huang, X., and Zhou, H.-X. (2006) Similarity and Difference in the Unfolding of Thermophilic and Mesophilic Cold Shock Proteins Studied by Molecular Dynamics Simulations. *Biophysical Journal.* 91, 2451-2463
63. Lasagna-Reeves, C. A., Castillo-Carranza, D. L., Sengupta, U., Guerrero-Munoz, M. J., Kiritoshi, T., Neugebauer, V., Jackson, G. R., and Kayed, R. (2012) Alzheimer brain-derived tau oligomers propagate pathology from endogenous tau. *Scientific Reports.* 2, 700
64. Shelton, L. B., Baker, J. D., Zheng, D., Sullivan, L. E., Solanki, P. K., Webster, J. M., Sun, Z., Sabbagh, J. J., Nordhues, B. A., Koren, J., Ghosh, S., Blagg, B. S. J., Blair, L. J., and Dickey, C. A. (2017) Hsp90 activator Aha1 drives production of pathological tau aggregates. *Proc. Natl. Acad. Sci. U.S.A.* 114, 9707-9712
65. Gerson, J. E., Sengupta, U., and Kayed, R. (2017) Tau Oligomers as Pathogenic Seeds: Preparation and Propagation In Vitro and In Vivo. *Methods Mol. Biol.* 1523, 141-157
66. Wilson, D. M., and Binder, L. I. (1997) Free fatty acids stimulate the polymerization of tau and amyloid beta peptides. In vitro evidence for a common effector of pathogenesis in Alzheimer's disease. *Am J Pathol.* 150, 2181-2195
67. von Bergen, M., Barghorn, S., Li, L., Marx, A., Biernat, J., Mandelkow, E. M., and Mandelkow, E. (2001) Mutations of tau protein in frontotemporal dementia promote aggregation of paired helical filaments by enhancing local beta-structure. *J Biol. Chem.* 276, 48165-48174
68. Ganguly, P., Do, T. D., Larini, L., LaPointe, N. E., Sercel, A. J., Shade, M. F., Feinstein, S. C., Bowers, M. T., and Shea, J.-E. (2015) Tau Assembly: The Dominant Role of PHF6 (VQIVYK) in Microtubule Binding Region Repeat R3. *J Phys Chem B.* 119, 4582-4593
69. Zheng, J., Liu, C., Sawaya, M. R., Vadla, B., Khan, S., Woods, R. J., Eisenberg, D., Goux, W. J., and Nowick, J. S. (2011) Macrocyclic-Sheet Peptides That Inhibit the Aggregation of a Tau-Protein-Derived Hexapeptide. *J Am. Chem. Soc.* 133, 3144-3157
70. Fitzpatrick, A. W. P., Falcon, B., He, S., Murzin, A. G., Murshudov, G., Garringer, H. J., Crowther, R. A., Ghetti, B., Goedert, M., and Scheres, S. H. W. (2017) Cryo-EM structures of tau filaments from Alzheimer's disease. *Nature.* 547, 185-190
71. Frenkel-Pinter, M., Richman, M., Belostozky, A., Abu-Mokh, A., Gazit, E., Rahimipour, S., and Segal, D. (2016) Selective Inhibition of Aggregation and Toxicity of a Tau-Derived Peptide using Its Glycosylated Analogues. *Chemistry.* 22, 5945-5952
72. Frenkel-Pinter, M., Tal, S., Scherzer-Attali, R., Abu-Hussien, M., Alyagor, I., Eisenbaum, T., Gazit, E., and Segal, D. (2017) Cl-NQTrp Alleviates Tauopathy Symptoms in a Model Organism through the Inhibition of Tau Aggregation-Engendered Toxicity. *Neurodegener Dis.* 17, 73-82
73. Fuchs, P. F. J., and Alix, A. J. P. (2005) High accuracy prediction of β-turns and their types using propensities and multiple alignments. *Proteins.* 59, 828-839
74. Permyakov, S. E., Permyakov, E. A., and Uversky, V. N. (2015) Intrinsically disordered caldesmon binds calmodulin via the "buttons on a string" mechanism. *PeerJ.* 3, e1265
75. Phadtare, S., Hwang, J., Severinov, K., and Inouye, M. (2003) CspB and CspL, thermostable coldshock proteins from *Thermotoga maritima*. *Genes Cells.* 8, 801-810

It will be apparent to those skilled in the art that various modifications and variations can be made in the present disclosure without departing from the scope or spirit of the invention. Other embodiments of the disclosure will be apparent to those skilled in the art from consideration of the specification and practice of the methods disclosed herein. It is intended that the specification and examples be considered as exemplary only, with a true scope and spirit of the invention being indicated by the following claims.

| SEQUENCES |
| --- |

SEQ ID NO: 1: *Thermotoga Maritima* cold-shock protein
MRGKVKWFDS KKGYGFITKD EGGDVFVHWS AIEMEGFKTL KEGQVVEFEI
QEGKKGPQAA HVKVVE SEQ ID NO: 2: <sup>Tm</sup>CSP-mutant Y14A, F16A, F26A, H28Q
MRGKVKWFDS KKAGAITKD EGGDVAVQWS AIEMEGFKTL KEGQVVEFEI
QEGKKGPQAA HVKVVE SEQ ID NO: 3: <sup>Tm</sup>CSP-Library L
MRGKVKWFDX XXGYGFITKD EGGDVFVHXX AIEMXXXKTL KEGQVVEFEI QEGKKGPQAA
HVKVVE SEQ ID NO: 4: <sup>Tm</sup>CSP-Library F
MRGKVXXFXS KKGXXXITKD EGGXVXVHWS AIEMEGFKTL KEGQVVEFEI
QEGKKGPQAA HVKVVE SEQ ID NO: 5: <sup>Tm</sup>CSP-Library K
MRGKVKWFDS KKGYGFITKD EGGDVFVHWS AIEMEGFKTL KEGQVVEFEI
XXXXXXXXAA HVKVVE SEQ ID NO: 6: Lin28B protein
MAEGGASKGG GEEPGKLPEP AEEESQVLRG TGHCKWFNVR MGFGFISMIN
REGSPLDIPV DVFVHQSKLF MEGFRSLKEG EPVEFTFKKS SKGLESIRVT
GPGGSPCLGS ERRPKGKTLQ KRKPKGDRCY NCGGLDHHAK ECSLPPQPKK
CHYCQSIMHM VANCPHKNVA QPPASSQGRQ EAESQPCTST LPREVGGGHG
CTSPPFPQEA RAEISERSGR SPQEASSTKS SIAPEEQSKK GPSVQKRKKT SEQ ID NO: 7: Lin28B-Cold Shock Domain
VLRGTGHCKW FNVRMGFGFI SMINREGSPL DIPVDVFVHQ SKLFMEGFRS LKEGEPVEFT
FKKSSKGLES IRVTG SEQ ID NO: 8: random <sup>Tm</sup>CSP clone 1 from Library L
MRGKVKWFDR AIGYGFITKD EGGDVFVHPP AIEMSGPKTL KEGQVVEFEI
QEGKKGPQAA HVKVVE SEQ ID NO: 9: random <sup>Tm</sup>CSP clone 2 from Library L
MRGKVKWFDD AQGYGFITKD EGGDVFVHSH AIEMMTGKTL KEGQVVEFEI
QEGKKGPQAA HVKVVE SEQ ID NO: 10: random <sup>Tm</sup>CSP clone 3 from Library L
MRGKVKWFDM TNGYGFITKD EGGDVFVHLK AIEMASPKTL KEGQVVEFEI
QEGKKGPQAA HVKVVE SEQ ID NO: 11: random <sup>Tm</sup>CSP clone 4 from Library L
MRGKVKWFDV LLGYGFITKD EGGDVFVHIA AIEMRMRKTL KEGQVVEFEI
QEGKKGPQAA HVKVVE SEQ ID NO: 12: random <sup>Tm</sup>CSP clone 5 from Library L
MRGKVKWFDL QRGYGFITKD EGGDVFVHTA AIEMQMAKTL KEGQVVEFEI
QEGKKGPQAA HVKVVE SEQ ID NO: 13: random <sup>Tm</sup>CSP clone 6 from Library L
MRGKVKWFDL TTGYGFITKD EGGDVFVHAL AIEMAGRKTL KEGQVVEFEI
QEGKKGPQAA HVKVVE SEQ ID NO: 14: random <sup>Tm</sup>CSP clone 7 from Library L
MRGKVKWFDP AVGYGFITKD EGGDVFVHPG AIEMKVLKTL KEGQVVEFEI
QEGKKGPQAA HVKVVE SEQ ID NO: 15: random <sup>Tm</sup>CSP clone 8 from Library L
MRGKVKWFDR ALGYGFITKD EGGDVFVHPR AIEMVTLKTL KEGQVVEFEI
QEGKKGPQAA HVKVVE SEQ ID NO: 16: random <sup>Tm</sup>CSP clone 9 from Library L
MRGKVKWFDA VMGYGFITKD EGGDVFVHIA AIEMHAEKTL KEGQVVEFEI
QEGKKGPQAA HVKVVE SEQ ID NO: 17: random <sup>Tm</sup>CSP clone 10 from Library L
MRGKVKWFDI DGGYGFITKD EGGDVFVHVI AIEMVGIKTL KEGQVVEFEI
QEGKKGPQAA HVKVVE SEQ ID NO: 18: random <sup>Tm</sup>CSP clone 11 from Library L
MRGKVKWFDD RPGYGFITKD EGGDVFVHKT AIEMPLLKTL KEGQVVEFEI
QEGKKGPQAA HVKVVE SEQ ID NO: 19: random <sup>Tm</sup>CSP clone 12 from Library L
MRGKVKWFDR EPGYGFITKD EGGDVFVHAA AIEMALPKTL KEGQVVEFEI
QEGKKGPQAA HVKVVE

SEQUENCES

SEQ ID NO: 20: random <sup>Tm</sup>CSP clone 13 from Library L
MRGKVKWFDD HGGYGFITKD EGGDVFVHHR AIEMRQTKTL KEGQVVEFEI
QEGKKGPQAA HVKVVE SEQ ID NO: 21: random <sup>Tm</sup>CSP clone 14 from Library L
MRGKVKWFDV AKGYGFITKD EGGDVFVHVV AIEMGPVKTL KEGQVVEFEI
QEGKKGPQAA HVKVVE SEQ ID NO: 22: random <sup>Tm</sup>CSP clone 15 from Library L
MRGKVKWFDH KPGYGFITKD EGGDVFVHQG AIEMDQRKTL KEGQVVEFEI
QEGKKGPQAA HVKVVE SEQ ID NO: 23: random <sup>Tm</sup>CSP clone 16 from Library L
MRGKVKWFDR KAGYGFITKD EGGDVFVHGV AIEMLVTKTL KEGQVVEFEI
QEGKKGPQAA HVKVVE SEQ ID NO: 24: random <sup>Tm</sup>CSP clone 17 from Library L
MRGKVKWFDM RVGYGFITKD EGGDVFVHQA AIEMLLTKTL KEGQVVEFEI
QEGKKGPQAA HVKVVE SEQ ID NO: 25: random <sup>Tm</sup>CSP clone 18 from Library L
MRGKVKWFDK KIGYGFITKD EGGDVFVHTS AIEMAMPKTL KEGQVVEFEI
QEGKKGPQAA HVKVVE SEQ ID NO: 26: random <sup>Tm</sup>CSP clone 19 from Library L
MRGKG*

SEQ ID NO: 27: random <sup>Tm</sup>CSP clone 20 from Library L
MRGKVKWFDG HHGYGFITKD EGGDVFVHQG AIEMRAQKTL KEGQVVEFEI
QEGKKGPQAA MRLLSEETSLRPHSSN*

SEQ ID NO: 28: random <sup>Tm</sup>CSP clone 21 from Library L
MRGKVKWFD- --GYGFITKD EGGDVFVHPA AIEMPDPKTL KEGQVVEFEI
QEGKKGPQAA HVKVVE SEQ ID NO: 29: <sup>Tm</sup>CSP-PHF6-11B-1
MRGKVKWFDS KKGYGFITKD EGGDVFVHWS AIEMEGFKTL KEGQVVEFEI
QVQIVYKG PGSKYVIQV QAAHVKVVE*

SEQ ID NO: 30: <sup>Tm</sup>CSP-PHF6-11B-2
MRGKVKWFDS KKGYGFITKD EGGDVFVHWS AIEMEGFKTL KEGQVVEFEI
QGVQIVYKG PGSKYVIQVG QAAHVKVVE*

SEQ ID NO: 31: PHF6
VQIVYK

SEQ ID NO: 32: PHF6*
VQIINK

SEQ ID NO: 33: <sup>Tm</sup>CSP-PHF6-1
MRGKVKWFDS KKGYGFITKD EGGDVFVHWS AIEMEGFKTL KEGQVVEFEI
QGVQIVYKG PSPKYVIQVG QAAHVKVVE*

SEQ ID NO: 34: FLAG-<sup>Tm</sup>CSP-PHF6-1
MDYKDDDDKR SGGSNSMRGK VKWFDSKKGY GFITKDEGGD VFVHWSAIEM
EGFKTLKEGQ VVEFEIQEGK KGPQAAHVKV VE*

SEQ ID NO: 35: CMA
MARVKKDQAEPLHRKFERQPPG

SEQ ID NO: 36: PEST-Degron
SHGFPPEVEEQDDGTLPMSCAQESGMDRHPAACASARI

I claim:

1. A recombinant binding protein scaffold comprising a fusion protein, wherein the fusion protein comprises a cold-shock protein and a peptide consisting of SEQ ID NO: 31 or SEQ ID NO: 32, wherein SEQ ID NO: 31 or SEQ ID NO: 32 replaces a binding domain of the cold-shock protein.

2. The recombinant binding protein scaffold of claim 1, wherein the cold-shock protein is derived from a thermophile or hyperthermophile microorganism.

3. The recombinant binding protein scaffold of claim 2, wherein the microorganism is *Thermotoga maritima*.

4. The recombinant binding protein scaffold of claim 1, wherein the recombinant binding protein comprises residues from cold shock protein from a microorganism and residues from a cold shock domain-containing protein from a human.

5. The recombinant binding protein scaffold of claim 1, wherein the cold-shock protein or cold shock domain does not comprise cysteine residues.

6. The recombinant binding protein scaffold of claim 3, wherein the cold-shock protein comprises at least 80% sequence identity to SEQ ID NO: 1.

7. The recombinant binding protein scaffold of claim 6, wherein SEQ ID NO: 1 is modified in at least one of these residues: Y14A, F16A, F26A, and H28Q, and comprises at least one further modification.

8. The recombinant binding protein scaffold of claim 1, wherein the binding domain comprises at least two amino acids mutations in positions 10, 11, 12, 29, 30, 35, 36, and 37 of SEQ ID NO: 1.

9. The recombinant binding protein scaffold of claim 1, wherein the binding domain comprises at least two amino acids mutations in positions 6, 7, 9, 14, 15, 16, 24, and 26 of SEQ ID NO: 1.

10. The recombinant binding protein scaffold of claim 1, wherein the binding domain comprises at least two amino acids mutations in positions 51, 52, 53, 54, 55, 56, 57, and 58 of SEQ ID NO: 1.

11. The recombinant binding protein scaffold of claim 1, wherein the binding domain binds a protein or peptide of interest.

12. The recombinant binding protein scaffold of claim 11, wherein the binding domain comprises an RGD sequence.

13. The recombinant binding protein scaffold of claim 12, wherein the RGD sequence binds integrin proteins.

* * * * *

SEQUENCE LISTING

<160> NUMBER OF SEQ ID NOS: 44

<210> SEQ ID NO 1
<211> LENGTH: 66
<212> TYPE: PRT
<213> ORGANISM: Thermotoga maritima
<220> FEATURE:
<223> OTHER INFORMATION: Description of sequence: Thermotoga Maritima
      cold-shock protein

<400> SEQUENCE: 1

Met Arg Gly Lys Val Lys Trp Phe Asp Ser Lys Lys Gly Tyr Gly Phe
1               5                   10                  15

Ile Thr Lys Asp Glu Gly Gly Asp Val Phe Val His Trp Ser Ala Ile
            20                  25                  30

Glu Met Glu Gly Phe Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 2
<211> LENGTH: 66
<212> TYPE: PRT
<213> ORGANISM: Artificial Sequence
<220> FEATURE:
<223> OTHER INFORMATION: Description of sequence: cold-shock protein
      sequence

<400> SEQUENCE: 2

Met Arg Gly Lys Val Lys Trp Phe Asp Ser Lys Lys Gly Ala Gly Ala
1               5                   10                  15

Ile Thr Lys Asp Glu Gly Gly Asp Val Ala Val Gln Trp Ser Ala Ile
            20                  25                  30

Glu Met Glu Gly Phe Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 3
<211> LENGTH: 66
<212> TYPE: PRT
<213> ORGANISM: Artificial Sequence
<220> FEATURE:
<223> OTHER INFORMATION: Description of sequence: Library peptide
<220> FEATURE:
<221> NAME/KEY: misc_feature
<222> LOCATION: (10)..(12)
<223> OTHER INFORMATION: Xaa can be any naturally occurring amino acid
<220> FEATURE:
<221> NAME/KEY: misc_feature
<222> LOCATION: (29)..(30)
<223> OTHER INFORMATION: Xaa can be any naturally occurring amino acid
<220> FEATURE:
<221> NAME/KEY: misc_feature
<222> LOCATION: (35)..(37)
<223> OTHER INFORMATION: Xaa can be any naturally occurring amino acid

<400> SEQUENCE: 3

Met Arg Gly Lys Val Lys Trp Phe Asp Xaa Xaa Xaa Gly Tyr Gly Phe
1               5                   10                  15

Ile Thr Lys Asp Glu Gly Gly Asp Val Phe Val His Xaa Xaa Ala Ile
            20                  25                  30

Glu Met Xaa Xaa Xaa Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu

```
<210> SEQ ID NO 4
<211> LENGTH: 66
<212> TYPE: PRT
<213> ORGANISM: Artificial Sequence
<220> FEATURE:
<223> OTHER INFORMATION: Description of sequence: Library peptide
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(16)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 4

Met Arg Gly Lys Val Xaa Xaa Phe Xaa Ser Lys Gly Xaa Xaa Xaa
1               5                   10                  15

Ile Thr Lys Asp Glu Gly Gly Xaa Val Xaa Val His Trp Ser Ala Ile
            20                  25                  30

Glu Met Glu Gly Phe Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 5
<211> LENGTH: 66
<212> TYPE: PRT
<213> ORGANISM: Artificial Sequence
<220> FEATURE:
<223> OTHER INFORMATION: Description of sequence: Library peptide
<220> FEATURE:
<221> NAME/KEY: misc_feature
<222> LOCATION: (51)..(58)
<223> OTHER INFORMATION: Xaa can be any naturally occurring amino acid

<400> SEQUENCE: 5

Met Arg Gly Lys Val Lys Trp Phe Asp Ser Lys Gly Tyr Gly Phe
1               5                   10                  15

Ile Thr Lys Asp Glu Gly Gly Asp Val Phe Val His Trp Ser Ala Ile
            20                  25                  30

Glu Met Glu Gly Phe Lys Thr Leu Lys Glu Gly Gln Val Val Glu Phe
        35                  40                  45

Glu Ile Xaa Xaa Xaa Xaa Xaa Xaa Xaa Xaa Ala Ala His Val Lys Val
    50                  55                  60

Val Glu
65

<210> SEQ ID NO 6
<211> LENGTH: 250
```

<212> TYPE: PRT
<213> ORGANISM: Artificial Sequence
<220> FEATURE:
<223> OTHER INFORMATION: Description of sequence: Lin28B protein

<400> SEQUENCE: 6

Met Ala Glu Gly Gly Ala Ser Lys Gly Gly Glu Glu Pro Gly Lys
1               5                   10                  15

Leu Pro Glu Pro Ala Glu Glu Ser Gln Val Leu Arg Gly Thr Gly
                20                  25                  30

His Cys Lys Trp Phe Asn Val Arg Met Gly Phe Gly Phe Ile Ser Met
                35                  40                  45

Ile Asn Arg Glu Gly Ser Pro Leu Asp Ile Pro Val Asp Val Phe Val
50                  55                  60

His Gln Ser Lys Leu Phe Met Glu Gly Phe Arg Ser Leu Lys Glu Gly
65                  70                  75                  80

Glu Pro Val Glu Phe Thr Phe Lys Lys Ser Lys Gly Leu Glu Ser
                85                  90                  95

Ile Arg Val Thr Gly Pro Gly Gly Ser Pro Cys Leu Gly Ser Glu Arg
                100                 105                 110

Arg Pro Lys Gly Lys Thr Leu Gln Lys Arg Lys Pro Lys Gly Asp Arg
                115                 120                 125

Cys Tyr Asn Cys Gly Gly Leu Asp His His Ala Lys Glu Cys Ser Leu
130                 135                 140

Pro Pro Gln Pro Lys Lys Cys His Tyr Cys Gln Ser Ile Met His Met
145                 150                 155                 160

Val Ala Asn Cys Pro His Lys Asn Val Ala Gln Pro Ala Ser Ser
                165                 170                 175

Gln Gly Arg Gln Glu Ala Glu Ser Gln Pro Cys Thr Ser Thr Leu Pro
                180                 185                 190

Arg Glu Val Gly Gly His Gly Cys Thr Ser Pro Pro Phe Pro Gln
                195                 200                 205

Glu Ala Arg Ala Glu Ile Ser Glu Arg Ser Gly Arg Ser Pro Gln Glu
210                 215                 220

Ala Ser Ser Thr Lys Ser Ser Ile Ala Pro Glu Glu Gln Ser Lys Lys
225                 230                 235                 240

Gly Pro Ser Val Gln Lys Arg Lys Lys Thr
                245                 250

<210> SEQ ID NO 7
<211> LENGTH: 75
<212> TYPE: PRT
<213> ORGANISM: Artificial Sequence
<220> FEATURE:
<223> OTHER INFORMATION: Description of sequence: Domain

<400> SEQUENCE: 7

Val Leu Arg Gly Thr Gly His Cys Lys Trp Phe Asn Val Arg Met Gly
1               5                   10                  15

Phe Gly Phe Ile Ser Met Ile Asn Arg Glu Gly Ser Pro Leu Asp Ile
                20                  25                  30

Pro Val Asp Val Phe Val His Gln Ser Lys Leu Phe Met Glu Gly Phe
                35                  40                  45

Arg Ser Leu Lys Glu Gly Glu Pro Val Glu Phe Thr Phe Lys Lys Ser
    50                  55                  60

Ser Lys Gly Leu Glu Ser Ile Arg Val Thr Gly
65                  70                  75

<210> SEQ ID NO 8
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 8

```
Met Arg Gly Lys Val Lys Trp Phe Asp Arg Ala Ile Gly Tyr Gly Phe
1               5                   10                  15

Ile Thr Lys Asp Glu Gly Gly Asp Val Phe Val His Pro Pro Ala Ile
            20                  25                  30

Glu Met Ser Gly Pro Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65
```

<210> SEQ ID NO 9
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 9

```
Met Arg Gly Lys Val Lys Trp Phe Asp Asp Ala Gln Gly Tyr Gly Phe
1               5                   10                  15

Ile Thr Lys Asp Glu Gly Gly Asp Val Phe Val His Ser His Ala Ile
            20                  25                  30

Glu Met Met Thr Gly Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65
```

<210> SEQ ID NO 10
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 10

```
Met Arg Gly Lys Val Lys Trp Phe Asp Met Thr Asn Gly Tyr Gly Phe
1               5                   10                  15

Ile Thr Lys Asp Glu Gly Gly Asp Val Phe Val His Leu Lys Ala Ile
            20                  25                  30

Glu Met Ala Ser Pro Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65
```

<210> SEQ ID NO 11
<211> LENGTH: 66

```
<212> TYPE: PRT
<213> ORGANISM: Artificial Sequence
<220> FEATURE:
<223> OTHER INFORMATION: Description of sequence: Library clone

<400> SEQUENCE: 11

Met Arg Gly Lys Val Lys Trp Phe Asp Val Leu Leu Gly Tyr Gly Phe
1               5                   10                  15

Ile Thr Lys Asp Glu Gly Gly Asp Val Phe Val His Ile Ala Ala Ile
            20                  25                  30

Glu Met Arg Met Arg Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 12
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 12

Met Arg Gly Lys Val Lys Trp Phe Asp Leu Gln Arg Gly Tyr Gly Phe
1               5                   10                  15

Ile Thr Lys Asp Glu Gly Gly Asp Val Phe Val His Thr Ala Ala Ile
            20                  25                  30

Glu Met Gln Met Ala Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 13
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 13

Met Arg Gly Lys Val Lys Trp Phe Asp Leu Thr Thr Gly Tyr Gly Phe
1               5                   10                  15

Ile Thr Lys Asp Glu Gly Gly Asp Val Phe Val His Ala Leu Ala Ile
            20                  25                  30

Glu Met Ala Gly Arg Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 14
<211> LENGTH: 66
<212> TYPE: PRT
<213> ORGANISM: Artificial Sequence
<220> FEATURE:
<223> OTHER INFORMATION: Description of sequence: Library clone
```

-continued

```
<400> SEQUENCE: 14

Met Arg Gly Lys Val Lys Trp Phe Asp Pro Ala Val Gly Tyr Gly Phe
1               5                   10                  15

Ile Thr Lys Asp Glu Gly Gly Asp Val Phe Val His Pro Gly Ala Ile
            20                  25                  30

Glu Met Lys Val Leu Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 15
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 15

Met Arg Gly Lys Val Lys Trp Phe Asp Arg Ala Leu Gly Tyr Gly Phe
1               5                   10                  15

Ile Thr Lys Asp Glu Gly Gly Asp Val Phe Val His Pro Arg Ala Ile
            20                  25                  30

Glu Met Val Thr Leu Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 16
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 16

Met Arg Gly Lys Val Lys Trp Phe Asp Ala Val Met Gly Tyr Gly Phe
1               5                   10                  15

Ile Thr Lys Asp Glu Gly Gly Asp Val Phe Val His Ile Ala Ala Ile
            20                  25                  30

Glu Met His Ala Glu Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 17
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 17

Met Arg Gly Lys Val Lys Trp Phe Asp Ile Asp Gly Gly Tyr Gly Phe
```

```
                1               5                   10                  15
Ile Thr Lys Asp Glu Gly Gly Asp Val Phe Val His Val Ile Ala Ile
                20                  25                  30

Glu Met Val Gly Ile Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 18
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 18

Met Arg Gly Lys Val Lys Trp Phe Asp Asp Arg Pro Gly Tyr Gly Phe
1               5                   10                  15

Ile Thr Lys Asp Glu Gly Gly Asp Val Phe Val His Lys Thr Ala Ile
                20                  25                  30

Glu Met Pro Leu Leu Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 19
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 19

Met Arg Gly Lys Val Lys Trp Phe Asp Arg Glu Pro Gly Tyr Gly Phe
1               5                   10                  15

Ile Thr Lys Asp Glu Gly Gly Asp Val Phe Val His Ala Ala Ala Ile
                20                  25                  30

Glu Met Ala Leu Pro Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 20
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 20

Met Arg Gly Lys Val Lys Trp Phe Asp Asp His Gly Gly Tyr Gly Phe
1               5                   10                  15

Ile Thr Lys Asp Glu Gly Gly Asp Val Phe Val His His Arg Ala Ile
                20                  25                  30
```

Glu Met Arg Gln Thr Lys Thr Leu Lys Glu Gly Gln Val Val Glu Phe
            35                  40                  45

Glu Ile Gln Glu Gly Lys Lys Gly Pro Gln Ala Ala His Val Lys Val
 50                  55                  60

Val Glu
 65

<210> SEQ ID NO 21
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 21

Met Arg Gly Lys Val Lys Trp Phe Asp Val Ala Lys Gly Tyr Gly Phe
 1               5                  10                  15

Ile Thr Lys Asp Glu Gly Gly Asp Val Phe Val His Val Val Ala Ile
            20                  25                  30

Glu Met Gly Pro Val Lys Thr Leu Lys Glu Gly Gln Val Val Glu Phe
            35                  40                  45

Glu Ile Gln Glu Gly Lys Lys Gly Pro Gln Ala Ala His Val Lys Val
 50                  55                  60

Val Glu
 65

<210> SEQ ID NO 22
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 22

Met Arg Gly Lys Val Lys Trp Phe Asp His Lys Pro Gly Tyr Gly Phe
 1               5                  10                  15

Ile Thr Lys Asp Glu Gly Gly Asp Val Phe Val His Gln Gly Ala Ile
            20                  25                  30

Glu Met Asp Gln Arg Lys Thr Leu Lys Glu Gly Gln Val Val Glu Phe
            35                  40                  45

Glu Ile Gln Glu Gly Lys Lys Gly Pro Gln Ala Ala His Val Lys Val
 50                  55                  60

Val Glu
 65

<210> SEQ ID NO 23
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 23

Met Arg Gly Lys Val Lys Trp Phe Asp Arg Lys Ala Gly Tyr Gly Phe
 1               5                  10                  15

Ile Thr Lys Asp Glu Gly Gly Asp Val Phe Val His Gly Val Ala Ile
            20                  25                  30

Glu Met Leu Val Thr Lys Thr Leu Lys Glu Gly Gln Val Val Glu Phe
            35                  40                  45

```
Glu Ile Gln Glu Gly Lys Lys Gly Pro Gln Ala Ala His Val Lys Val
    50                  55                  60

Val Glu
65

<210> SEQ ID NO 24
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 24

Met Arg Gly Lys Val Lys Trp Phe Asp Met Arg Val Gly Tyr Gly Phe
1               5                   10                  15

Ile Thr Lys Asp Glu Gly Gly Asp Val Phe Val His Gln Ala Ala Ile
            20                  25                  30

Glu Met Leu Leu Thr Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 25
<211> LENGTH: 66
<212> TYPE: PRT
<213> ORGANISM: Artificial Sequence
<220> FEATURE:
<223> OTHER INFORMATION: Description of sequence: Library clone

<400> SEQUENCE: 25

Met Arg Gly Lys Val Lys Trp Phe Asp Lys Lys Ile Gly Tyr Gly Phe
1               5                   10                  15

Ile Thr Lys Asp Glu Gly Gly Asp Val Phe Val His Thr Ser Ala Ile
            20                  25                  30

Glu Met Ala Met Pro Lys Thr Leu Lys Glu Gly Gln Val Val Glu Phe
        35                  40                  45

Glu Ile Gln Glu Gly Lys Lys Gly Pro Gln Ala Ala His Val Lys Val
    50                  55                  60

Val Glu
65

<210> SEQ ID NO 26
<211> LENGTH: 5
<212> TYPE: PRT
<213> ORGANISM: Artificial Sequence
<220> FEATURE:
<223> OTHER INFORMATION: Description of sequence: Library clone

<400> SEQUENCE: 26

Met Arg Gly Lys Gly
1               5

<210> SEQ ID NO 27
<211> LENGTH: 76
<212> TYPE: PRT
<213> ORGANISM: Artificial Sequence
<220> FEATURE:
<223> OTHER INFORMATION: Description of sequence: Library clone

<400> SEQUENCE: 27
```

```
Met Arg Gly Lys Val Lys Trp Phe Asp Gly His His Gly Tyr Gly Phe
1               5                   10                  15

Ile Thr Lys Asp Glu Gly Gly Asp Val Phe Val His Gln Gly Ala Ile
            20                  25                  30

Glu Met Arg Ala Gln Lys Thr Leu Lys Glu Gly Gln Val Val Glu Phe
            35                  40                  45

Glu Ile Gln Glu Gly Lys Lys Gly Pro Gln Ala Ala Met Arg Leu Leu
        50                  55                  60

Ser Glu Glu Thr Ser Leu Arg Pro His Ser Ser Asn
65                  70                  75
```

<210> SEQ ID NO 28
<211> LENGTH: 63
<212> TYPE: PRT
<213> ORGANISM: Artificial Sequence
<220> FEATURE:
<223> OTHER INFORMATION: Description of sequence: Library clone

<400> SEQUENCE: 28

```
Met Arg Gly Lys Val Lys Trp Phe Asp Gly Tyr Gly Phe Ile Thr Lys
1               5                   10                  15

Asp Glu Gly Gly Asp Val Phe Val His Pro Ala Ala Ile Glu Met Pro
            20                  25                  30

Asp Pro Lys Thr Leu Lys Glu Gly Gln Val Val Glu Phe Glu Ile Gln
            35                  40                  45

Glu Gly Lys Lys Gly Pro Gln Ala Ala His Val Lys Val Val Glu
        50                  55                  60
```

<210> SEQ ID NO 29
<211> LENGTH: 76
<212> TYPE: PRT
<213> ORGANISM: Artificial Sequence
<220> FEATURE:
<223> OTHER INFORMATION: Description of sequence: peptide, Name: TmCSP-WT

<400> SEQUENCE: 29

```
Met Arg Gly Lys Val Lys Trp Phe Asp Ser Lys Lys Gly Tyr Gly Phe
1               5                   10                  15

Ile Thr Lys Asp Glu Gly Gly Asp Val Phe Val His Trp Ser Ala Ile
            20                  25                  30

Glu Met Glu Gly Phe Lys Thr Leu Lys Glu Gly Gln Val Val Glu Phe
            35                  40                  45

Glu Ile Gln Val Gln Ile Val Tyr Lys Gly Pro Gly Ser Lys Tyr Val
        50                  55                  60

Ile Gln Val Gln Ala Ala His Val Lys Val Val Glu
65                  70                  75
```

<210> SEQ ID NO 30
<211> LENGTH: 78
<212> TYPE: PRT
<213> ORGANISM: Artificial Sequence
<220> FEATURE:
<223> OTHER INFORMATION: Description of sequence: CSP WT protein sequence

<400> SEQUENCE: 30

```
Met Arg Gly Lys Val Lys Trp Phe Asp Ser Lys Lys Gly Tyr Gly Phe
1               5                   10                  15

Ile Thr Lys Asp Glu Gly Gly Asp Val Phe Val His Trp Ser Ala Ile
            20                  25                  30
```

```
Glu Met Glu Gly Phe Lys Thr Leu Lys Glu Gly Gln Val Val Glu Phe
            35                  40                  45

Glu Ile Gln Gly Val Gln Ile Val Tyr Lys Gly Pro Gly Ser Lys Tyr
        50                  55                  60

Val Ile Gln Val Gly Gln Ala Ala His Val Lys Val Val Glu
65                  70                  75
```

<210> SEQ ID NO 31
<211> LENGTH: 6
<212> TYPE: PRT
<213> ORGANISM: Artificial Sequence
<220> FEATURE:
<223> OTHER INFORMATION: Description of sequence: peptide, Name: PHF6
      sequence

<400> SEQUENCE: 31

```
Val Gln Ile Val Tyr Lys
1               5
```

<210> SEQ ID NO 32
<211> LENGTH: 6
<212> TYPE: PRT
<213> ORGANISM: Artificial Sequence
<220> FEATURE:
<223> OTHER INFORMATION: Description of sequence: peptide, Name: PHF6
      sequence

<400> SEQUENCE: 32

```
Val Gln Ile Ile Asn Lys
1               5
```

<210> SEQ ID NO 33
<211> LENGTH: 78
<212> TYPE: PRT
<213> ORGANISM: Artificial Sequence
<220> FEATURE:
<223> OTHER INFORMATION: Description of sequence: peptide, Name:
      TmCSP-PHF6-1

<400> SEQUENCE: 33

```
Met Arg Gly Lys Val Lys Trp Phe Asp Ser Lys Gly Tyr Gly Phe
1               5                   10                  15

Ile Thr Lys Asp Glu Gly Gly Asp Val Phe Val His Trp Ser Ala Ile
            20                  25                  30

Glu Met Glu Gly Phe Lys Thr Leu Lys Glu Gly Gln Val Val Glu Phe
            35                  40                  45

Glu Ile Gln Gly Val Gln Ile Val Tyr Lys Gly Pro Ser Pro Lys Tyr
        50                  55                  60

Val Ile Gln Val Gly Gln Ala Ala His Val Lys Val Val Glu
65                  70                  75
```

<210> SEQ ID NO 34
<211> LENGTH: 82
<212> TYPE: PRT
<213> ORGANISM: Artificial Sequence
<220> FEATURE:
<223> OTHER INFORMATION: Description of sequence: Peptide, name:
      FLAG-TmCSP-PHF6-1

<400> SEQUENCE: 34

```
Met Asp Tyr Lys Asp Asp Asp Lys Arg Ser Gly Gly Ser Asn Ser
1               5                   10                  15

Met Arg Gly Lys Val Lys Trp Phe Asp Ser Lys Lys Gly Tyr Gly Phe
```

```
                    20                  25                  30

Ile Thr Lys Asp Glu Gly Gly Asp Val Phe Val His Trp Ser Ala Ile
            35                  40                  45

Glu Met Glu Gly Phe Lys Thr Leu Lys Glu Gly Gln Val Val Glu Phe
        50                  55                  60

Glu Ile Gln Glu Gly Lys Lys Gly Pro Gln Ala Ala His Val Lys Val
65                  70                  75                  80

Val Glu

<210> SEQ ID NO 35
<211> LENGTH: 22
<212> TYPE: PRT
<213> ORGANISM: Artificial Sequence
<220> FEATURE:
<223> OTHER INFORMATION: Description of sequence: Signal peptide

<400> SEQUENCE: 35

Met Ala Arg Val Lys Lys Asp Gln Ala Glu Pro Leu His Arg Lys Phe
1               5                   10                  15

Glu Arg Gln Pro Pro Gly
            20

<210> SEQ ID NO 36
<211> LENGTH: 40
<212> TYPE: PRT
<213> ORGANISM: Artificial Sequence
<220> FEATURE:
<223> OTHER INFORMATION: Description of sequence: Signal peptide

<400> SEQUENCE: 36

Ser His Gly Phe Pro Pro Glu Val Glu Glu Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40

<210> SEQ ID NO 37
<211> LENGTH: 12
<212> TYPE: PRT
<213> ORGANISM: Artificial sequence
<220> FEATURE:
<223> OTHER INFORMATION: Description of sequence: Cold shock protein

<400> SEQUENCE: 37

Glu Ile Gln Glu Gly Lys Lys Gly Pro Gln Ala Ala
1               5                   10

<210> SEQ ID NO 38
<211> LENGTH: 22
<212> TYPE: PRT
<213> ORGANISM: Artificial sequence
<220> FEATURE:
<223> OTHER INFORMATION: Description of sequence: Cold shock protein

<400> SEQUENCE: 38

Glu Ile Gln Val Gln Ile Val Tyr Lys Gly Pro Gly Ser Lys Tyr Val
1               5                   10                  15

Ile Gln Val Gln Ala Ala
            20

<210> SEQ ID NO 39
```

```
<211> LENGTH: 24
<212> TYPE: PRT
<213> ORGANISM: Artificial sequence
<220> FEATURE:
<223> OTHER INFORMATION: Description of sequence: Cold shock protein

<400> SEQUENCE: 39

Glu Ile Gln Gly Val Gln Ile Val Tyr Lys Gly Pro Gly Ser Lys Tyr
1               5                   10                  15

Val Ile Gln Val Gly Gln Ala Ala
            20

<210> SEQ ID NO 40
<211> LENGTH: 18
<212> TYPE: PRT
<213> ORGANISM: Artificial sequence
<220> FEATURE:
<223> OTHER INFORMATION: Description of sequence: orientation
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 40

Xaa Val Gln Ile Val Tyr Lys Xaa Xaa Xaa Xaa Lys Tyr Val Ile Gln
1               5                   10                  15

Val Xaa

<210> SEQ ID NO 41
<211> LENGTH: 18
<212> TYPE: PRT
<213> ORGANISM: Artificial sequence
<220> FEATURE:
<223> OTHER INFORMATION: Description of sequence: orientation
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(11)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 41

Xaa Lys Tyr Val Ile Gln Val Xaa Xaa Xaa Xaa Val Gln Ile Val Tyr
1               5                   10                  15

Lys Xaa

<210> SEQ ID NO 42
<211> LENGTH: 4
<212> TYPE: PRT
<213> ORGANISM: Artificial sequence
<220> FEATURE:
<223> OTHER INFORMATION: Description of sequence: beta-turn type

<400> SEQUENCE: 42

Gly Pro Ser Gly
```

```
<210> SEQ ID NO 43
<211> LENGTH: 4
<212> TYPE: PRT
<213> ORGANISM: Artificial sequence
<220> FEATURE:
<223> OTHER INFORMATION: Description of sequence: beta-turn type

<400> SEQUENCE: 43

Gly Pro Gly Ser

<210> SEQ ID NO 44
<211> LENGTH: 4
<212> TYPE: PRT
<213> ORGANISM: Artificial sequence
<220> FEATURE:
<223> OTHER INFORMATION: Description of sequence: beta-turn type

<400> SEQUENCE: 44

Gly Gly Gly Gly
```